United States Patent [19]

Inoue et al.

[11] Patent Number: 5,387,684
[45] Date of Patent: Feb. 7, 1995

[54] ISOINDAZOLE COMPOUND

[75] Inventors: Yoshihisa Inoue; Hajime Ebisu; Norifumi Nakamura, all of Hirakata; Yoshitomi Morizawa, Yokohama; Takashi Okazoe, Yokohama; Arata Yasuda, Yokohama, all of Japan

[73] Assignees: The Green Cross Corporation, Osaka; Asahi Glass Co., Ltd., Tokyo, both of Japan

[21] Appl. No.: 142,447

[22] Filed: Jan. 24, 1994

[30] Foreign Application Priority Data

Mar. 25, 1992 [JP] Japan .................................. 4-98913
Jun. 10, 1992 [JP] Japan ................................. 4-176189
Mar. 25, 1993 [WO] WIPO ................. PCT/JP93/00354

[51] Int. Cl.6 .................. C07D 473/40; C07D 471/02; C07D 403/06
[52] U.S. Cl. .................................... 544/264; 546/118; 548/362.5
[58] Field of Search ...................... 546/118; 548/362.5; 544/264; 514/266, 303, 394

[56] References Cited

U.S. PATENT DOCUMENTS

| | | | |
|---|---|---|---|
| 4,048,182 | 9/1977 | Denzel | 546/118 |
| 4,859,684 | 8/1989 | Raeymaekers | 514/314 |
| 5,110,818 | 5/1992 | Allgeier | 514/261 |
| 5,173,494 | 12/1992 | Chiu | 514/303 |

*Primary Examiner*—C. Warren Ivy
*Assistant Examiner*—D. Margaret M. Mach
*Attorney, Agent, or Firm*—Sughrue, Mion, Zinn, Macpeak & Seas

[57] ABSTRACT

An isoindazole compound of the formula (1) or a salt thereof; a method for the production thereof; and pharmaceutical use of the compound and a salt thereof, particularly as an angiotensin II antagonist and as an agent for the prophylaxis and treatment of circulatory diseases (particularly hypertension and heart failure);

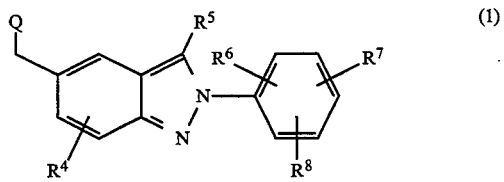

wherein Q is a heterocyclic derivative of the formula (2) or (3)

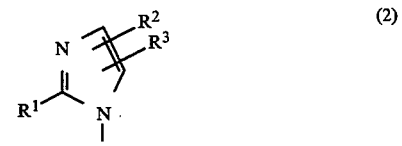

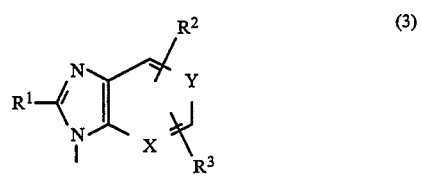

wherein other symbols of the above formulas are as defined in the Specification. The compound and its salt show superior angiotensin II antagonism and are low toxic. Accordingly, they are useful as angiotensin II antagonists for the treatment or prophylaxis of angiotensin II-mediated diseases such as circulatory diseases of hypertension (e.g. essential hypertension, renal hypertension) and heart failure.

17 Claims, No Drawings

ISOINDAZOLE COMPOUND

TECHNICAL FIELD

The present invention relates to a novel isoindazole (i.e. 2H-indazole) compound and its salt having superior pharmacological action. More particularly, the present invention relates to a novel isoindazole compound and its salt having angiotensin II antagonism and useful as a prophylactic and a therapeutic agent for circulatory diseases such as hypertension and heart failure.

BACKGROUND ART

The blood pressure of living organisms is adjusted by the sympathetic nervous system and the balance between the pressor system and the antihypertensive system. Deeply concerned with the pressor system is the renin-angiotensin system. Renin acts on angiotensinogen to produce angiotensin I. The angiotensin I is further converted to angiotensin II by an angiotensin converting enzyme. The angiotensin II has a strong vasoconstriction action, as well as acts on adrenal cortex to promote secretion of aldosterone, thereby increasing blood pressure. Since angiotension II acts via angiotensin II receptor on cell membranes, an antagonist thereof can, like an inhibitor of angiotensin converting enzyme, be used as a therapeutic agent for hypertension caused by angiotensin II.

While there have hitherto been known peptide angiotensin II antagonists represented by Saralasin, they are not effective by oral administration since they are peptide agents. However, there have recently reported nonpeptide angiotensin II antagonists (e.g. Japanese Patent Unexamined Publication Nos. 71074/1981, 501020/1991, 95181/1991, 236377/1991, 271288/1991), and they have been confirmed to be effective by oral administration.

Accordingly, an object of the present invention is to provide a nonpeptide compound having superior angiotensin II antagonism, which is efficacious by oral administration.

DISCLOSURE OF THE INVENTION

The present inventors have conducted intensive studies so as to achieve the aforementioned object, and now found that a novel isoindazole (2H-indazole) compound of the following formula (1) and its salt have superior angiotensin II antagonism and are efficacious by oral administration.

That is, the present invention relates to a novel isoindazole compound of the formula (1) [hereinafter sometimes referred to as isoindazole compound (1)] and its salt.

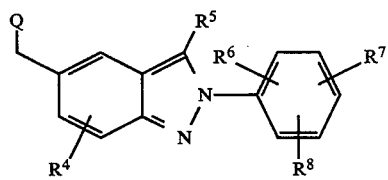

wherein Q is a heterocyclic derivative of the formula (2) or (3).

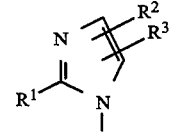

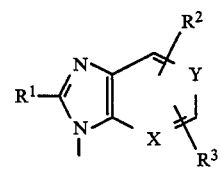

In the formulas (1), (2), and (3), $R^1$–$R^8$, X, and Y stand for the following.

$R^1$: lower alkyl, halo-lower alkyl, cyclo-lower alkyl, alkenyl, alkoxyl, alkoxy-lower alkyl, or alkylthio.

$R^2$ and $R^3$: They may be the same or different, and each is independently hydrogen atom, halogen atom, lower alkyl, halo-lower alkyl, cyclo-lower alkyl, alkenyl, alkoxyl, —$C_mF_{2m+1}$, —$(CH_2)_nR^9$, or —$(CH_2)_pCOR^{10}$.

$R^4$ and $R^5$: They may be the same or different, and each is independently hydrogen atom, halogen atom, lower alkyl, alkoxyl, or —$C_mF_{2+1}$.

$R^6$: carboxyl, —$COOR^{11}$, —$CONH_2$, cyano —$SO_3H$, —$SO_2NH_2$, —$NHSO_2CF_3$, or C-bonded tetrazolyl.

$R^7$ and $R^8$: They may be the same or different, and each is independently hydrogen atom, halogen atom, lower alkyl, alkoxyl, or —$C_mF_{2m+1}$.

X and Y: They may be the same or different, and each is independently CH or nitrogen atom.

In the aforementioned definitions, $R^9$–$R^{11}$, m, n, and p designate the following.

$R^9$: hydroxyl or alkoxyl $R^{10}$: hydrogen atom, hydroxyl, lower alkyl, or alkoxyl $R^{11}$: lower alkyl, alkenyl, cyclo-lower alkyl, aryl, or aralkyl m: an integer of 1–6 n: an integer of 1–4 p: an integer of 0–4

The present invention also relates to a method for producing isoindazole compound (1) and its salt, which comprises reacting a compound of the formula (4) with a compound of the formula (5) or (6).

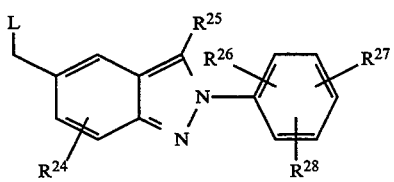

wherein L is a leaving group, and $R^{24}$, $R^{25}$, $R^{26}$, $R^{27}$, and $R^{28}$ are the same as the corresponding $R^4$, $R^5$, $R^6$, $R^7$, and $R^8$, respectively, in the formula (1), or the groups which can convert to the corresponding $R^4$, $R^5$, $R^6$, $R^7$, and $R^8$, respectively.

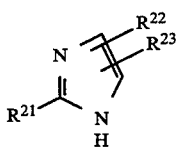

(5)

wherein $R^{21}$, $R^{22}$, and $R^{23}$ are the same as the corresponding $R^1$, $R^2$, and $R^3$, respectively, in the formula (2), or the groups which can convert to the corresponding $R^1$, $R^2$, and $R^3$, respectively.

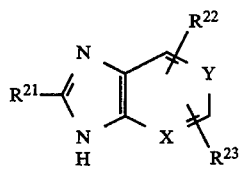

(6)

wherein $R^{21}$, $R^{22}$, and $R^{23}$ are the same as the corresponding $R^1$, $R^2$, and $R^3$, respectively, in the formula (3), or the groups which can convert to the corresponding $R^1$, $R^2$, and $R^3$, respectively.

The invention also relates to a pharmaceutical composition containing said isoindazole compound (1) or its salt, and pharmaceutically acceptable carriers; an angiotensin II antagonist containing, as an active ingredient, said isoindazole compound (1) or its salt; and to an agent for the prophylaxis and treatment of circulatory diseases (particularly hypertension and heart failure) containing, as an active ingredient, said isoindazole compound (1) or its salt.

The salts of the isoindazole compound (1) include, for example, acid addition salts derived from isoindazole compound (1) and inorganic acid or organic acid. Examples of such salt include hydrochloride, hydrobromide, sulfate, phosphate, methanesulfonate, p-toluenesulfonate, oxalate, tartrate, citrate, maleate, fumarate, succinate, lactate, glutarate, acetate, trifluoroacetate, and various salts of amino acid.

Besides, there are included salts formed from the isoindazole compound (1) and a base. Such salts may include salts formed from alkali metals such as sodium and potassium, alkaline earth metals such as calcium and magnesium, and ammonium or substituted ammonium such as dimethylammonium and triethylammonium.

In the present specification, "lower" organic group means that the group has 1 to 6 carbon atoms.

The lower alkyl at $R^1$–$R^5$, $R^7$, $R^8$, $R^{10}$, and $R^{11}$ may be straight or branched, and includes, for example, methyl, ethyl, propyl, isopropyl, butyl, isobutyl, t-butyl, pentyl, and hexyl.

The halo-lower alkyl at $R^1$–$R^3$ is a lower alkyl substituted by halogen (e.g. fluorine, chlorine, bromine, iodine) and may be straight or branched. Examples thereof include chloromethyl, 2-chloroethyl, bromomethyl, 2-bromoethyl, 1,2-dichloroethyl, 1,2-dibromoethyl, and 3-trifluoromethylpropyl.

The cyclo-lower alkyl at $R^1$–$R^3$ and $R^{11}$ is a cycloalkyl having 3 to 6 carbon atoms that constitutes a ring, and is exemplified by cyclopropyl, cyclobutyl, cyclopentyl, and cyclohexyl.

The alkenyl at $R^1$–$R^3$, and $R^{11}$ is preferably lower alkenyl, and more preferably has 2 to 4 carbon atoms. It may be straight or branched, and is exemplified by vinyl, allyl, 1-propenyl, isopropenyl, and 1-butenyl.

The alkoxyl at $R^1$–$R^5$, and $R^7$–$R^{10}$ is preferably lower alkoxyl, and more preferably has 1 to 4 carbon atoms. It may be straight or branched, and is exemplified by methoxy, ethoxy, propoxy, and butoxy.

The alkoxy-lower alkyl at $R^1$ may be straight or branched, and its alkoxyl moiety is preferably lower alkoxyl. Examples thereof include methoxyethyl, 3-methoxypropyl, and 2-ethoxyethyl.

The alkylthio at $R^1$ is preferably lower alkylthio, and more preferably has 1 to 4 carbon atoms. It may be straight or branched, and is exemplified by methylthio, ethylthio, propylthio, and butylthio.

The halogen atom at $R^2$–$R^5$, $R^7$, and $R^8$ means fluorine atom, chlorine atom, bromine atom, or iodine atom.

The aryl at $R^{11}$ is a monovalent aromatic hydrocarbon which may have a substituent such as halogen, lower alkoxyl, or lower alkylamino, and is preferably phenyl or its derivative. Examples thereof include phenyl, tolyl, p-halophenyl such as p-chlorophenyl and p-bromophenyl, alkoxyphenyl such as methoxyphenyl and ethoxyphenyl, and dialkylaminophenyl such as dimethylaminophenyl and diethylaminophenyl.

The aralkyl at $R^{11}$ is alkyl substituted by aryl exemplified supra. The alkyl preferably has 1 to 4 carbon atoms and is exemplified by benzyl, benzhydryl, trityl, and phenetyl.

The leaving group represented by L is, for example, chlorine, bromine, iodine, methanesulfonyloxy, or p-toluenesulfonyloxy.

The groups at $R^{21}$–$R^{28}$ which can convert to $R^1$–$R^8$ are exemplified by those identical with $R^1$–$R^8$ except that the functional group is protected by a protecting group, amino, protected amino, mercapto, and protected mercapto.

The position of the substituents $R^2$–$R^4$, and $R^6$–$R^8$ in the formulas (1), (2), and (3) is not subject to any particular limitation, but $R^6$ is preferably at the ortho position relative to the binding site. The same applies to the position of the substituents $R^{22}$–$R^{24}$, and $R^{26}$–$R^{28}$ in the formulas (4), (5), and (6).

Preferable isoindazole compound (1) includes
(1) the compound of the formula (1) wherein Q is a heterocyclic derivative of the formula (2), $R^1$ is lower alkyl or alkenyl, $R^2$ is chlorine atom, and $R^3$ is —$(CH_2)_nR^9$ or —$(CH_2)_pCOR^{10}$ (in which $R^9$ is hydroxyl or alkoxyl, $R^{10}$ is hydrogen atom, hydroxyl, or alkoxyl, n is an integer of 1–4, and p is an integer of 0–4); and
(2) the compound of the formula (1) wherein Q is a heterocyclic derivative of the formula (3), $R^1$ is lower alkyl or alkenyl, $R^2$ and $R^3$ may be the same or different and each is independently hydrogen atom, halogen atom, lower alkyl, —$(CH_2)_nR^9$, or —$(CH_2)_pCOR^{10}$ (in which $R^9$ is hydroxyl or alkoxyl, $R^{10}$ is hydrogen atom, hydroxyl, or alkoxyl, n is an integer of 1–4, and p is an integer of 0–4), X is nitrogen atom, Y is CH, $R^4$ is hydrogen atom, $R^5$ is hydrogen atom or halogen atom, $R^6$ is carboxyl or C-bonded tetrazolyl, and $R^7$ and $R^8$ may be the same or different and each is independently hydrogen atom, fluorine atom, chlorine atom, lower alkyl, or alkoxyl.

More preferable isoindazole compound (1) includes
(3) the compound of the formula (1) wherein Q is a heterocyclic derivative of the formula (2), $R^1$ is lower alkyl, $R^2$ is chlorine atom, $R^3$ is —$(CH_2)_nR^9$ or —$(CH_2)_pCOR^{10}$ (in which $R^9$ is hydroxyl, $R^{10}$ is hydrogen atom, hydroxyl, or alkoxyl, n is 1, and p is 0 or 1), $R^4$ is hydrogen atom, $R^5$ is hydrogen atom, fluorine atom, chlorine atom, or bromine atom, $R^6$ is carboxyl or C-bonded tetrazolyl, and $R^7$ and $R^8$ may be the same or different and each is independently hydrogen atom, fluorine atom, chlorine atom, or lower alkyl; and (4) the compound of the formula (1) wherein Q is a heterocyclic derivative of the formula (3), $R^1$ is lower alkyl, $R^2$ and $R^3$ may be the same or different and each is independently hydrogen atom, lower alkyl, —$(CH_2)_n R^9$ or —$(CH_2)_p COR^{10}$ (in which $R^9$ is hydroxyl, $R^{10}$ is hydrogen atom, hydroxyl, or alkoxyl, n is 1, and p is 0 or 1), $R^4$ is hydrogen atom, $R^5$ is hydrogen atom, fluorine atom, chlorine atom, or bromine atom, $R^6$ is carboxyl or C-bonded tetrazolyl, $R^7$ and $R^8$ may be the same or different and each is independently hydrogen atom, fluorine atom, chlorine atom, or lower alkyl, X is nitrogen atom, Y is CH.

When Q of the formula (1) is represented by the formula (3), it is particularly preferable that the total carbon number of the substituents for $R^1$, $R^2$ and $R^3$ should be 4.

The isoindazole compound (1) is produced by the method exemplified in the following.

A first method comprises conversion of the compounds of the formula (1): Method (A). A second method comprises conversion of an analogous compound to a compound of the formula (1) [the analogous compound has different substituent, etc. but has the same skeleton as that of the compound of the formula (I), hereinafter meaning the same]: Method (B). A third method comprises synthesis of a compound of the formula (1) or its analogue via two or more reactions of intermediate compounds: Method (C). The analogous compound obtained in (C) is converted to a compound of the formula (1) by Method (B). This Method (C) is concerned with the reaction for forming the skeleton.

Method (A) includes, for example, the following methods.

The compound of the formula (1) wherein $R^6$ is carboxyl can be obtained by hydrolysis of the compound of the formula (1) wherein $R^6$ is —$COOR^{11}$.

One method for obtaining the compound of the formula (1) wherein $R^6$ is C-bonded tetrazolyl comprises reacting a compound of the formula (1) wherein $R^6$ is cyano with a suitable azide compound such as sodium azide, ammonium azide (preferably prepared in situ from sodium azide and ammonium chloride), or tributyltin azide (preferably prepared in situ from sodium azide and tributyltin chloride) in an anhydrous solvent such as toluene, xylen, dimethoxyethane, or tetrahydrofuran at a refluxing temperature of the solvent or a nearby temperature. When tributyltin azide is used, the tributyltin group is removed by treating the resultant compound with a basic aqueous solution or acidic aqueous solution after the reaction.

Another method for obtaining the compound of the formula (1) wherein $R^6$ is C-bonded tetrazolyl comprises converting carboxyl of a compound of the formula (1) wherein $R^6$ is carboxyl to acid chloride or activated ester according to the method of J. V. Duncia et al [J. Org. Chem., 56, 2395 (1991)], then reacting the resulting compound with 2-aminopropionitrile, and then reacting the compound with triphenylphosphine, diethyl azodicarboxylate, and trimethylsilyl azide.

Method (B) is typically carried out by converting functional groups and substituents. In this method, a compound of the formula (1) is synthesized by converting functional groups and substituents of an analogous compound having the same skeleton as that of the compound of the formula (1) but having functional groups and substituents outside the scope of the compound of the formula (1).

A typical conversion of functional group, etc. comprises deprotection of a functional group protected by a protecting group. Also, the compound of the formula (1) can be synthesized from an analogous compound having amino or mercapto at the position corresponding to $R^6$, by converting said amino or mercapto to the group defined by $R^6$. Examples of such method (B) include the following.

A compound of the formula (1) wherein $R^6$ is C-bonded tetrazolyl can be obtained by subjecting an analogous compound having, at the position corresponding to $R^6$, C-bonded tetrazolyl protected by a suitable protecting group to deprotection. The protecting group in this case includes, for example, triphenylmethyl and cyanoethyl. The deprotection may be a conventional one such as that described in, for example, T. W. Greene, "Protective Groups in Organic Synthesis" [John Wiley and Sons, Inc. (1981)].

A compound of the formula (1) wherein $R^6$ is —$NHSO_2CF_3$ can be obtained by reacting an analogous compound having amino at the position corresponding to $R^6$ with trifluoromethanesulfonic anhydride in a suitable solvent such as dichloromethane in the presence of a suitable base such as triethylamine.

The analogous compound having amino at the position corresponding to $R^6$ can be synthesized by Curtius rearrangement from a compound of the formula (1) wherein $R^6$ is carboxyl, by using, upon protection of other functional groups with suitable protecting group where necessary, diphenylphosphoryl azide in an alcohol solvent such as t-butyl alcohol in the presence of a base such as triethylamine to give a carbamate, and subjecting said carbamate to acid hydrolysis by the reaction with hydrochloric acid in a solvent such as ethanol.

A compound of the formula (1) wherein $R^6$ is —$SO_3H$ can be produced from an analogous compound having mercapto at the position corresponding to $R^6$, by oxidizing the mercapto with a suitable oxidizing agent such as hydrogen peroxide, m-chloroperoxybenzoic acid, or potassium permanganate. The analogous compound having mercapto at the position corresponding to $R^6$ can be synthesized by, for example, the following method (C).

The method (C) accompanies the reaction for forming the skeleton, by which .the compound of the formula (1) and its analogue can be obtained. The typical skeleton-forming reaction is the reaction of a compound of the formula (4) with a compound of the formula (5) or (6).

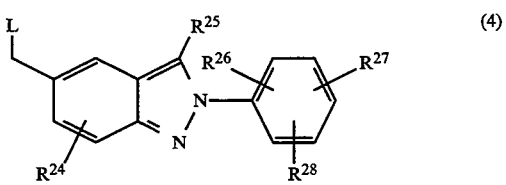
(4)

wherein L and $R^{24}$–$R^{28}$ are as defined above.

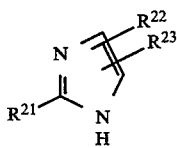

wherein $R^{21}$-$R^{23}$ are as defined above.

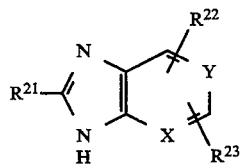

wherein $R^{21}$-$R^{23}$ are as defined above.

The skeleton of the isoindazole compound (1) is formed by reacting a compound of the formula (4) with an imidazole of the formula (5) or imidazopyridine of the formula (6) in an aprotic solvent such as N,N-dimethylformamide, N,N-dimethylacetamide, tetrahydrofuran, or dioxane in the presence of a base such as sodium hydride, sodium carbonate, potassium carbonate, or sodium methoxide at a temperature between 0° C. and the refluxing temperature of the solvent.

When synthesizing the isoindazole compound (1), $R^1$-$R^8$ are not necessarily the same throughout the synthesis from the starting material to the final product. There are occasions when the conversion exemplified below is required to introduce the final product.

The method (C) will be explained by referring to an intermediate compound wherein $R^{21}$-$R^{28}$ save $R^{26}$ are the same as the corresponding $R^1$-$R^8$ (excluding $R^6$) in formula (1).

The isoindazole compound of the formula (1) wherein $R^6$ is C-bonded tetrazolyl can be obtained by reacting a compound of the formula (4) wherein $R^{26}$ is protected C-bonded tetrazolyl with imidazole of the formula (5) or imidazopyridine of the formula (6) in an aprotic solvent such as N,N-dimethylformamide, N,N-dimethylacetamide, tetrahydrofuran, or dioxane in the presence of a base such as sodium hydride, sodium carbonate, potassium carbonate, or sodium methoxide at a temperature between 0° C. and the refluxing temperature of the solvent.

Alternatively, said compound can be obtained by reacting a compound of the formula (4) wherein $R^{26}$ is protected C-bonded tetrazolyl with imidazole of the formula (5) or imidazopyridine of the formula (6) in a mixed solvent of a basic aqueous solution such as an aqueous solution of sodium hydroxide or potassium hydroxide and a suitable organic solvent such as methylene chloride in the presence of a phase transfer catalyst (e.g. Aliquat 336) such as tetraalkylammonium salt at a temperature between 0° C. and the refluxing temperature of the solvent.

The intermediate compound of the formula (4) can be produced, for example, by converting the 5-position methyl of the compound of the formula (7) to —CH$_2$L (L is a leaving group as defined above).

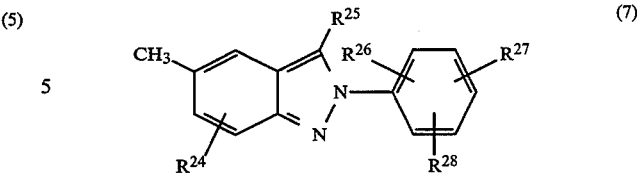

wherein $R^{24}$-$R^{28}$ are as defined above.

While the substituents in the formula (7) were defined to be the same as those in the formula (4) (namely, $R^{24}$-$R^{28}$ are common for the two formulas), the substituents may be other than those insofar as they can be converted to the corresponding $R^4$-$R^8$ in the formula (1). Similarly in the formulas (8)-(10) to be mentioned later, the substituents are conveniently supposed to be the same as those in the formula (4).

For example, when L is chlorine, bromine, or iodine, the compound of the formula (7) is reacted with N-chlorosuccinimide, N-bromosuccinimide, or N-iodosuccinimide in the presence of a radical initiator such as azobisisobutyronitrile or dibenzoyl peroxide to convert same to a compound of the formula (4). A similar reaction can be performed by irradiation of light instead of using the aforementioned radical initiator.

When $R^{25}$ of the compound of the formula (4) is chlorine, bromine, or iodine, L and $R^{25}$ may be the same, and they can be made chlorine, bromine, or iodine at the same time by reacting a compound of the formula (7) wherein $R^{25}$ is hydrogen atom under the same reaction conditions as those described above.

The compound of the formula (7) can be produced by reacting a compound of the formula (8) with a deoxygenating agent such as triethyl phosphite.

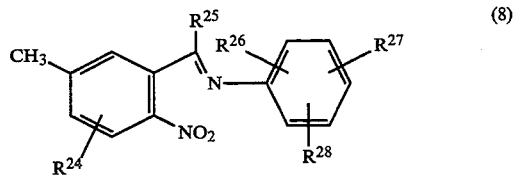

wherein $R^{24}$-$R^{28}$ are as defined above.

A compound of the formula (7) wherein $R^{26}$ is C-bonded tetrazolyl protected by a suitable protecting group such as triphenylmethyl or cyanoethyl can be synthesized from a compound of the formula (7) wherein $R^{26}$ is cyano by converting its substituent.

For example, it can be obtained by reacting a compound of the formula (7) wherein $R^{26}$ is cyano with a suitable azide compound such as sodium azide, ammonium azide (preferably prepared in situ from sodium azide and ammonium chloride), or tributyltin azide (preferably prepared in situ from sodium azide and tributyltin chloride) in an anhydrous solvent such as toluene, xylen, dimethoxyethane, or tetrahydrofuran at a refluxing temperature of the solvent or a nearby temperature (when tributyltin azide is used, the tributyltin is removed by treating the resultant compound with an aqueous basic solution or aqueous acidic solution after the reaction), and attaching a protecting group thereto.

Alternatively, a compound of the formula (7) wherein $R^{26}$ is C-bonded tetrazolyl protected by a suitable protecting group such as triphenylmethyl or cyanoethyl can be obtained according to J. V. Duncia et al [J. Org. Chem., 56, 2895 (1991)], by synthesizing from a compound of the formula (7) wherein $R^{26}$ is carboxyl. That is, it can be obtained by converting carboxyl at $R^{26}$ to acid chloride or activated ester, reacting the resulting compound with 2-aminopropionitrile, further reacting same with triphenyl phosphine, diethyl azodicarboxylate, and trimethylsilyl azide, and then attaching a protecting group.

The compound of the formula (8) can be obtained by reacting a compound of the formula (9) with a compound of the formula (10) in a suitable solvent such as benzene or toluene in the presence of a dehydrating agent such as Molecular Sieves or while removing moisture by azeotropic dehydration.

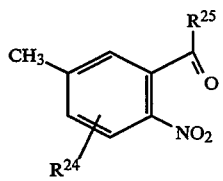
(9)

wherein $R^{24}$ and $R^{25}$ are as defined above.

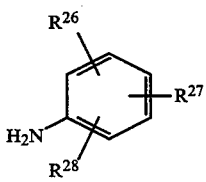
(10)

$R^{26}$ wherein $R^{26}$–$R^{28}$ are as defined above. The compound of the formula (9) can be synthesized according to, for example, the method of T. G. Miller et al [J. Org. Chem., 45, 1384 (1980)].

Of the compounds of the formula (10), the compound wherein $R^{26}$ is C-bonded tetrazolyl protected by a suitable protecting group such as triphenylmethyl or cyanoethyl can be obtained by protecting amino of a compound of the formula (10) wherein $R^{26}$ is cyano with a suitable protecting group, reacting the compound with a suitable azide compound such as sodium azide, ammonium azide (preferably prepared in situ from sodium azide and ammonium chloride), or tributyltin azide (preferably prepared in situ from sodium azide and tributyltin chloride) in an anhydrous solvent such as toluene, xylen, dimethoxyethane, or tetrahydrofuran at a refluxing temperature of the solvent or a nearby temperature (when tributyltin azide is used, the tributyltin is removed by treating the resultant compound with a basic aqueous solution or acidic aqueous solution after the reaction), attaching a suitable protecting group to the resultant tetrazole, and deprotection of the amino.

Of the compounds of the formula (10), a compound wherein $R^{26}$ is C-bonded tetrazolyl protected by a suitable protecting group such as triphenylmethyl or cyanoethyl can be obtained according to J. V. Duncia et al [J. Org. Chem., 56, 2395 (1991)] by protecting the amino of a compound of the formula (10) wherein $R^{26}$ is carboxyl with a suitable protecting group, converting the carboxyl to acid chloride or activated ester, reacting the resulting compound with 2-aminopropionitrile, further reacting same with triphenyl phosphine, diethyl azodicarboxylate, and trimethylsilyl azide, attaching a suitable protecting group to the resultant tetrazole, and then deprotecting the amino.

The imidazole of the formula (5) can be synthesized, for example, according to the method of Japanese Patent Unexamined Publication No. 501020/1991 or a method analogous thereto.

The imidazopyridine of the formula (6) can be synthesized, for example, according to the method of Japanese Patent Unexamined Publication No. 95181/1991 or a method analogous thereto.

The isoindazole compound (1) of the present invention can be isolated and purified by a conventional means such as extraction, crystallization, fractional crystallization, recrystallization, and chromatography.

The isoindazole compound (1) thus obtained can be converted to its salt by a conventional method.

The isoindazole compound (1) and its salt of the present invention show superior angiotensin II antagonism and are low toxic. Accordingly, they are useful as angiotensin II antagonists to be used for the treatment or prophylaxis of angiotensin II-mediated diseases such as circulatory diseases of hypertension (e.g. essential hypertension, renal hypertension) and heart failure.

The isoindazole compound (1) and its salt of the present invention are expected to be useful as a prophylactic and/or a therapeutic agent for heart disorders such as angina pectoris, arrhythmia, and cardiac infarction, aldosteronism, cerebral circulartory diseases, senile dementia, eye diseases such as glaucoma, and so on, as well as diagnostics for the tests of the renin-angiotensin system.

For treatment or prophylaxis, the isoindazole compound (1) or its salt of the present invention is used in the form of a conventional pharmaceutical preparation containing the isoindazole compound (1) or its salt (which is the active ingredient) in admixture with pharmaceutically acceptable carriers (organic or inorganic, solid or liquid excipients and the like suitable for oral, parenteral, or external use). The pharmaceutical preparation may be in a solid state such as tablet, granule, powder, or capsule, or in a liquid state such as liquid preparation, suspension, syrup, lotion, and lemonade.

Where necessary, auxiliaries, stabilizers, wetting agents, other conventional additives such as lactose, citric acid, tartaric acid, stearic acid, magnesium stearate, terra abla, sucrose, corn starch, talc, gelatin, agar, pectin, peanut oil, olive oil, cacao oil, and ethylene glycol, and the like may be added to the pharmaceutical preparation.

While the dose of the isoindazole compound (1) or its salt may vary depending on age, symptom, kind of disease and conditions of patients, the kind of isoindazole compound (1) or its salt to be used, and so on, it is generally administered daily at 0.01 mg —about 500 mg. When treating various diseases, the isoindazole compound (1) or its salt of the present invention may be used at an average dose of about 0.05 mg, 0.1 mg, 0.25 mg, 0.5 mg, 1 mg, 20 mg, 50 mg, or 100 mg.

The present invention is detailedly explained in the following by way of examples, to which the invention is not limited.

Reference Example 1

Synthesis of 5-methyl-2-nitrobenzaldehyde

Pyridinium chlorochromate (25.0 g, 116 mmol) was added to methylene chloride (65 ml) while stirring, and then thereto was added 5-methyl-2-nitrobenzyl alcohol (12.9 g, 77.3 mmol). The mixture was stirred at room temperature for 15 hours, and diethyl ether (155 ml) was added. The ether layer was removed by decantation.

Diethyl ether (30 ml) was added to the residue, and the ether layer was removed by decantation (3 times). The ether layers were combined, and passed through 15.5 g of silica gel. The obtained solution was concentrated, and subjected to flash chromatography on silica gel using a mixed solvent of hexane/ethyl acetate (8:1), whereby 10.6 g of 5-methyl-2-nitrobenzaldehyde was obtained.

NMR (270 MHz, CDCl$_3$) δ 10.44 (s, 1H); 8.04 (d, J=8.4 Hz, 1H); 7.73 (s, 1H); 7.55 (d, J=8.4 Hz, 1H); 2.52 (s, 3H)

Reference Example 2

Synthesis of ethyl N-(5-methyl-2-nitrobenzylidene)anthranilate

To 5-methyl-2-nitrobenzaldehyde (4.26 g, 25.8 mmol) as obtained in Reference Example 1 was added toluene (30 ml), and the mixture was stirred. Thereto was added ethyl anthranilate (4.26 g, 25.8 mmol). After the mixture was refluxed under heating for 10 hours, it was allowed to cool. Then, Molecular Sieves 5A (20.6 g) was added and the mixture was left standing overnight. The mixture was filtered, and the cake was washed 5 times with 20 ml of toluene. The filtrate was concentrated, added with 25 ml of toluene for dissolution, and added with hexane (25 ml) while stirring. The precipitated solid was filtered off, and washed twice with 30 ml of a mixed solvent of toluene/hexane (1:2). The cake was dried in vacuo to give 3.11 g of ethyl N-(5-methyl-2-nitrobenzylidene)anthranilate.

NMR (270 MHz, CDCl$_3$) δ 8.79 (s, 1H); 7.03–8.14 (m, 7H); 4.35 (q, J=7.0 Hz, 2H); 2.53 (s, 3H); 1.35 (t, J=7.0 Hz, 3H)

Reference Example 3

Synthesis of ethyl 2-(5-methyl-2H-indazol-2-yl)benzoate

Triethyl phosphite (5.8 ml, 34 mmol) was added to ethyl N-(5-methyl-2-nitrobenzylidene)anthranilate (3.10 g, 9.93 mmol) as obtained in Reference Example 2. The mixture was refluxed under heating for 4 hours, and the triethyl phosphite was evaporated under reduced pressure. The residue was purified by flash chromatography on silica gel using a mixed solvent of hexane/ethyl acetate (5:1), whereby 1.79 g of ethyl 2-(5-methyl-2H-indazol-2-yl)benzoate was obtained.

NMR (270 MHz, CDCl$_3$) δ 8.08 (s, 1H); 7.14–7.92 (m, 7H); 4.06 (q, J=7.0 Hz, 2H); 2.44 (s, 3H); 0.88 (t, J=7.0 Hz, 3H)

Reference Example 4

Synthesis of ethyl 2-(3-bromo-5-methyl-2H-indazol-2-yl)benzoate

Carbon tetrachloride (26 ml) was added to ethyl 2-(5-methyl-2H-indazol-2-yl)benzoate (1.43 g, 5.10 mmol) as obtained in Reference Example 3 and the mixture was stirred. Thereto were added N-bromosuccinimide (0.908 g, 5.10 mmol) and azobisisobutyronitrile (78 mg, 0.48 mmol), and the mixture was refluxed under heating for 3 hours. After cooling, the mixture was filtered, and the cake was washed twice with carbon tetrachloride (5 ml). The filtrate was concentrated, and subjected to flash chromatography on silica gel using a mixed solvent of hexane/ethyl acetate (8:1–3:1), whereby 1.47 g of ethyl 2-(3-bromo-5-methyl-2H-indazol-2-yl)benzoate was obtained.

NMR (270 MHz, CDCl$_3$) δ 7.2–8.2 (m, 7H); 4.0 (q, J=7 Hz, 2H); 2.4 (s, 3H ); 0.8 (t, J=7 Hz, 3H )

Reference Example 5

Synthesis of ethyl 2-[3-bromo-5-(bromomethyl)-2-H-indazol-2-yl]benzoate

Carbon tetrachloride (130 ml) was added to ethyl 2-(5-methyl-2H-indazol-2-yl)benzoate (7.14 g, 25.5 mmol) as obtained in Reference Example 3, and then thereto was added N-bromosuccinimide (4.62 g, 26.0 mmol). The mixture was stirred for 6 hours, and N-bromosuccinimide (0.36 g, 2.04 mmol) was added. After 1 hour of reaction, N-bromosuccinimide (4.54 g, 25.5 mmol) and azobisisobutyronitrile (0.21 g, 1.275 mmol) were added thereto, and the mixture was refluxed for 3.5 hours, followed by cooling. Dichloromethane (260 ml ) and water (130 ml) were added thereto to partition the solution, and the water layer was extracted with dichloromethane (65 ml). The organic layer was washed with water (130 ml), dried over magnesium sulfate, and filtered. The filtrate was concentrated by an evaporator. The residue was subjected to flash chromatography on silica gel using a mixed solvent of hexane/ethyl acetate (8:1), whereby 1.95 g of ethyl 2-[3-bromo-5-(bromomethyl)-2H-indazol-2-yl]benzoate was obtained.

NMR (270 MHz, CDCl$_3$) δ 8.2 (m, 1H); 7.4–7.7 (m, 6H); 4.6 (s, 2H); 4.0 (q, J=8 Hz, 2H); 0.8 (t, J=8 Hz, 3H)

Reference Example 6

Synthesis of 2-[N-(5-methyl-2-nitrobenzylidene)amino]benzonitrile

Toluene (167 ml) and 2-aminobenzonitrile (19.7 g, 167 mmol) were added to 5-methyl-2-nitrobenzaldehyde (27.5 g, 167 mmol) as obtained in Reference Example 1, and the mixture was stirred and refluxed for 14 hours, followed by cooling. The resultant crystals were filtered off, washed with a mixed solvent of hexane/toluene (2:1, 150 ml) and hexane (150 ml) twice to give 27.5 g of 2-[N-(5-methyl-2-nitrobenzylidene)amino]benzonitrile. In addition, the solid precipitated from the filtrate was filtered off and washed with hexane (100 ml and 50 ml) to give 10.0 g of the compound.

NMR (270 MHz, CDCl$_3$) δ 9.0 (s, 1H); 8.2 (s, 1H); 7.2–8.1 (m, 6H); 2.5 (s, 3H)

Reference Example 7

Synthesis of 2-(5-methyl-2H-indazol-2-yl)benzonitrile

To 2-[N-(5-methyl-2-nitrobenzylidene)amino]benzonitrile (37.5 g, 141 mmol) as obtained in Reference Example 6 was added triethyl phosphite (82.8 ml, 483 mmol), and the mixture was refluxed for 3 hours and allowed to cool. The resultant solid was filtered off, washed twice with ethyl acetate (80 ml) and twice with methanol (80 ml), and dried in vacuo to give 10.2 g of 2-(5-methyl-2H-indazol-2-yl)benzonitrile.

NMR (270 MHz, CDCl$_3$) δ 8.5 (s, 1H); 7.2–8.0 (m, 7H); 2.4 (s, 3H)

Reference Example 8

Synthesis of 5-[2-(5-methyl-2H-indazol-2-yl )phenyl]-2-(triphenylmethyl)-2H-tetrazole To 2-(5-methyl-2H-indazol-2-yl)benzonitrile (3.53 g, 15.1 mmol) as obtained in Reference Example 7 was added toluene (11.3 ml), and the mixture was stirred. Thereto were further added sodium azide (0.982 g, 15.1 mmol) and tributyltin chloride (4.46 ml, 16.4 mmol), and the mixture was refluxed under heating for 45 hours. The mixture was allowed to cool, and diluted with toluene (4 ml). 10N Aqueous sodium hydroxide (1.8 ml) and trityl chloride (4.36 g, 15.6 mmol) were added thereto while stirring. Water (10 ml) was added and the mixture was stirred at room temperature for 1.5 hours, and then added with hexane (20 ml). The solid was filtered off, and sequentially washed twice with water (15 ml), a mixed solvent of hexane/toluene (2:1, 15 ml), and hexane (15 ml). The cake was dried in vacuo to give 8.0 g of 5-[2-(5-methyl-2H-indazol-2-yl)phenyl]-2-(triphenylmethyl)-2H-tetrazole.
NMR (270 MHz, CDCl$_3$) δ 8.1 (m, 1H); 7.8 (s, 1H); 6.8–7.6 (m, 21H); 2.4 (s, 3H)

Reference Example 9

Synthesis of 5-{2-[3-bromo-5-(bromomethyl)-2H-indazol-2-yl]-phenyl}-2-(triphenylmethyl)-2H-tetrazole
To 5-[2-(5-methyl-2H-indazol-2-yl)phenyl]-2-(triphenylmethyl)-2H-tetrazole (14.5 g, 30.0 mmol) as obtained in Reference Example 8 was treated in the same manner as in Reference Example 5 to give 3.67 g of 5-{2-[3-bromo-5-(bromomethyl)-2H-indazol-2-yl]phenyl}-2-(triphenylmethyl)-2H-tetrazole.
NMR (270 MHz, CDCl$_3$) δ 8.5 (d, J=8 Hz, 1H); 6.8–7.7 (m, 21H); 4.6 (s, 2H)

Example 1

Syntheses of 2-butyl-4-chloro-1-[3-bromo-2-(2-ethoxycarbonylphenyl)-2H-indazol-5-yl]methyl-1H-imidazole-5-carbaldehyde and 2-butyl-4-chloro-1-[2-(2-ethoxycarbonylphenyl)-2H-indazol-5-yl]methyl-1H-imidazole-5-carbaldehyde To ethyl 2-(5-methyl-2H-indazol-2-yl)benzoate (0.95 g, 3.4 mmol) as obtained in Reference Example 3 was added carbon tetrachloride (17 ml), and then thereto were added N-bromosuccinimide (0.60 g, 3.4 mmol) and azobisisobutyronitrile (56 mg, 0.34 mmol). After the mixture was allowed to react under refluxing for 3 hours, it was cooled, and added with N-bromosuccinimide (0.12 g, 0.68 mmol) and azobisisobutyronitrile (11 mg, 0.068 mmol). The mixture was refluxed for 1.5 hours, and allowed to cool. The mixture was filtered and the filtrate was concentrated by an evaporator. The residue was dissolved in N,N-dimethylformamide (8 ml), added with 2-butyl-4-chloro-1H-imidazole-5-carbaldehyde (0.45 g, 2.4 mmol) and potassium carbonate (0.37 g, 2.6 mmol), and stirred at room temperature for two days. The mixture was filtered, and the cake was washed twice with chloroform (5 ml). The N,N-dimethylformamide was evaporated from the filtrate, and the residue was subjected to flash chromatography on silica gel using a mixed solvent of hexane/ethyl acetate (3:1–2:1), whereby 0.22 g of 2-butyl-4-chloro-1-[3-bromo-2-(2-ethoxycarbonylphenyl)-2H-indazol-5-yl]methyl-1H-imidazole-5-carbaldehyde and 0.20 g of 2-butyl-4-chloro-1-[2-(2-ethoxycarbonylphenyl)-2H-indazol-5-yl]methyl-1H-imidazole- 5-carbaldehyde were obtained.
NMR (270 MHz, CDCl$_3$)
 2-butyl-4-chloro-1-[3-bromo-2-(2-ethoxycarbonylphenyl)-2H-indazol-5-yl]methyl-1H-imidazole-5-carbaldehyde: δ 9.8 (s, 1H); 7.1–8.2 (m, 7H); 5.6 (s, 2H); 4.0 (q, J=7 Hz, 2H); 2.7 (t, J=8 Hz, 2H); 1.7 (m, 2H); 1.3 (m, 2H); 0.9 (t, J=7 Hz, 3H); 0.8 (t, J=7 Hz, 3H)
 2-butyl-4-chloro-1-[2-(2-ethoxycarbonylphenyl)-2H-indazol-5-yl]methyl-1H-imidazole-5-carbaldehyde: δ 9.8 (s, 1H); 8.2 (s, 1H); 7.1–7.9 (m, 7H); 5.6 (s, 2H); 4.0 (q, J=7 Hz, 2H); 2.7 (t, J=8 Hz, 2H); 1.7 (m, 2H); 1.3 (m, 2H); 0.9 (m, 6H)

Example 2

Synthesis of 1-[3-bromo-2-(2-ethoxycarbonylphenyl)-2H-indazol-5-yl]methyl-2-butyl-4-chloro-5-(hydroxymethyl)-1H-imidazole
2-Butyl-4-chloro-1-[3-bromo-2-(2-ethoxycarbonylphenyl)-2H-indazol-5-yl]methyl-1H-imidazole-5-carbaldehyde (0.122 g, 0.224 mmol) as obtained in Example 1 was dissolved in a mixed solvent of tetrahydrofuran (1.2 ml) and methanol (1.2 ml), and the mixture was stirred. Thereto was added sodium borohydride (8.5 mg, 0.224 mmol), and the mixture was allowed to react at room temperature for 5 minutes. The mixture was concentrated by an evaporator, and partitioned by a saturated aqueous solution of sodium hydrogencarbonate (2.5 ml) and ethyl acetate (2.5 ml). The organic layer was separated, and further, the water layer was extracted with ethyl acetate (2.5 ml). The organic layers were combined, dried over magnesium sulfate, and then filtered.
The solvent was evaporated in vacuo to give 0.110 g of 1-[3-bromo-2-(2-ethoxycarbonylphenyl)-2H-indazol-5-yl]methyl-2-butyl-4-chloro-5-(hydroxymethyl)-1H-imidazole.
NMR (270MHz, CDCl$_3$) δ 7.1–8.2 (m, 7H); 5.3 (s, 2H); 4.6 (s, 2H); 4.0 (q, J=7 Hz, 2H); 2.9 (bs, 1H); 2.6 (t, J=8 Hz, 2H); 1.7 (m, 2H); 1.3 (m, 2H); 0.9 (t, J=7 Hz, 3H); 0.8 (t, J=7 Hz, 3H)

Example 3

Synthesis of 2-butyl-4-chloro-1-[2-(2-ethoxycarbonylphenyl)-2H-indazol-5-yl]methyl-5-(hydroxymethyl)-1H-imidazole
2-Butyl-4-chloro-1-[2-(2-ethoxycarbonylphenyl)-2H-indazol-5-yl]methyl-1H-imidazole-5-carbaldehyde (0.133 g, 0.286 mmol) as obtained in Example 1 was dissolved in a mixed solvent of tetrahydrofuran (1.5 ml) and methanol (1.5 ml), and the mixture was stirred. Thereto was added sodium borohydride (11 mg, 0.286 mmol), and the mixture was allowed to react at room temperature for 5 minutes. The mixture was concentrated in an evaporator, and partitioned by a saturated aqueous solution of sodium hydrogencarbonate (3 ml) and ethyl acetate (3 ml). The organic layer was separated, and further, the water layer was extracted with ethyl acetate (3 ml). The organic layers were combined, dried over magnesium sulfate, and then filtered. The solvent was evaporated in vacuo to give 0.116 g of 2-butyl-4-chloro-1-[2-(2-ethoxycarbonylphenyl)-2H-indazol-5-yl]methyl-5-(hydroxymethyl)-1H-imidazole.
NMR (270MHz, CDCl$_3$) δ 8.1 (s, 1H); 7.1–8.0 (m, 7H); 5.3 (s, 2H); 4.6 (s, 2H); 4.0 (q, J=7 Hz, 2H); 2.8 (bs, 1H); 2.6 (t, J=8 Hz, 2H); 1.7 (m, 2H); 1.4 (m, 2H); 0.9 (m, 6H)

Example 4

Synthesis of 1-[3-bromo-2-(2-carboxyphenyl)-2H-indazol-5-yl]methyl-2-butyl-4-chloro-5-(hydroxymethyl)-1H-imidazole
Ethanol (1.2 ml), ion-exchanged water (0.3 ml), and potassium hydroxide (45 mg) were added to 1-[3-bromo-2-(2-ethoxycarbonylphenyl)-2H-indazol-5-yl]methyl-2-butyl-4-chloro-5-(hydroxymethyl)-1H-imidazole (106 mg, 0.205 mmol) as obtained in Example 2, and the mixture was stirred at room temperature for one day. The mixture was concentrated in an evaporator, and partitioned by ion-exchanged water (2.5 ml) and diethyl ether (5 ml). The water layer was separated and conc. hydrochloric acid was dropwise added thereto to adjust its pH to 5–6. The resultant solid was filtered off and washed twice with ion-exchanged water (1 ml). One drop of conc. hydrochloric acid was added to the filtrate to precipitate solid, which was filtered off, washed with water, and combined with the previously-obtained solid. They were dried in vacuo at 37° C. for two days to give 56 mg of 1-[3-bromo-2-(2-carboxyphenyl)-2H-indazol-5-yl]methyl-2-butyl-4-chloro-5-(hydroxymethyl)-1-H-imidazole.

NMR (270 MHz, Acetone-$d_6$) δ 7.2–8.2 (m, 7H); 5.4 (s, 2H); 4.6 (s, 2H); 4.4 (bs, 1H); 2.6 (t, J=8 Hz, 2H); 1.6 (m, 2H); 1.4 (m, 2H); 0.8 (t, J=7 Hz, 3H)

Example 5

Synthesis of 2-butyl-4-chloro-1-[2-(2-carboxyphenyl)-2H-indazol-5-yl]methyl-5-(hydroxymethyl)-1H-imidazole Ethanol (1.5 ml), ion-exchanged water (0.3 ml), and potassium hydroxide (42 mg) were added to 2-butyl-4-chloro-1-[2-(2-ethoxycarbonylphenyl)-2H-indazol-5-yl]methyl-5-(hydroxymethyl)-1H-imidazole (116 mg, 0.248 mmol) as obtained in Example 3, and the mixture was stirred at room temperature for 1.5 hours. The mixture was concentrated in an evaporator, and partitioned by ion-exchanged water (2.5 ml) and diethyl ether (5 ml). The water layer was separated and conc. hydrochloric acid was dropwise added thereto to adjust its pH to 2. The resultant solid was filtered off and washed three times with ion-exchanged water (1 ml). The solid was dried in vacuo at 37° C. overnight to give 58 mg of 2-butyl-4-chloro-1-[2-(2-carboxyphenyl)-2H-indazol-5-yl]methyl-5-(hydroxymethyl)-1H-imidazole.

NMR (270 MHz, Acetone-$d_6$) δ 8.5 (s, 1H); 7.2–8.0 (m, 7H); 5.4 (s, 2H); 4.5 (s, 2H); 4.3 (bs, 1H); 2.6 (t, J=7 Hz, 2H); 1.6 (m, 2H); 1.3 (m, 2H); 0.8 (t, J=7 Hz, 3H)

Example 6

Synthesis of 2-butyl-4-chloro-1-[3-bromo-2-(2-carboxyphenyl)-2H-indazol-5-yl]methyl-1H-imidazole-5-carbaldehyde Ethanol (1.2 ml), ion-exchanged water (0.3 ml), and potassium hydroxide (28 mg) were added to 2-butyl-4-chloro-1-[3-bromo-2-(2-ethoxycarbonylphenyl)-2H-indazol-5-yl]methyl-1 H-imidazole-5-carbaldehyde (101 mg, 0.186 mmol) as obtained in Example 1, and the mixture was stirred at room temperature for one day. The mixture was concentrated in an evaporator, and partitioned by ion-exchanged water (2.5 ml) and diethyl ether (5 ml). The water layer was separated and conc. hydrochloric acid was dropwise added thereto to adjust its pH to 5. The resultant solid was filtered off and washed three times with ion-exchanged water (1 ml). The solid was dried in vacuo overnight at 37° C. to give 72 mg of 2-butyl-4-chloro-1-[3-bromo-2-(2-carboxyphenyl)-2H-indazol-5-yl]methyl-1H-imidazole-5-carbaldehyde.

NMR (270 MHz, Acetone-$d_6$) δ 9.7 (s, 1H); 7.1–8.1 (m, 7H); 5.6 (s, 2H); 2.7 (t, J=7 Hz, 2H); 1.6 (m, 2H); 1.3 (m, 2H); 0.8 (t, J=7 Hz, 3H)

Example 7

Synthesis of 2-butyl-4-chloro-1-[2-(2-carboxyphenyl)-2H-indazol-5-yl]methyl-1H-imidazole-5-carbaldehyde Ethanol (0.8 ml), ion-exchanged water (0.2 ml), and potassium hydroxide (28 mg) were added to 2-butyl-4-chloro-1-[2-(2-ethoxycarbonylphenyl)-2H-indazol-5-yl]methyl-1H-imidazole-5-carbaldehyde (61 mg, 0.13 mmol) as obtained in Example 1, and the mixture was stirred at room temperature for 2 hours. The mixture was concentrated in an evaporator, and partitioned by ion-exchanged water (2.5 ml) and diethyl ether (5 ml). The water layer was separated and conc. hydrochloric acid was dropwise added thereto to adjust its pH to 1. The resultant solid was filtered off and washed three times with ion-exchanged water (1 ml). It was then dried in vacuo overnight at 37° C. to give 36 mg of 2-butyl-4-chloro-1-[2-(2-carboxyphenyl)-2H-indazol-5-yl]methyl-1H-imidazole-5-carbaldehyde.

NMR (270 MHz, Acetone-$d_6$) δ 9.8 (s, 1H); 8.5 (s, 1H); 7.2–8.0 (m, 7H); 5.8 (s, 2H); 2.8 (t, J=8 Hz, 2H); 1.7 (m, 2H); 1.4 (m, 2H ); 0.8 (t, J=7 Hz, 3H )

Example 8

Syntheses of methyl 2-butyl-4-chloro-1-[3-bromo-2-(2-ethoxycarbonylphenyl)-2H-indazol-5-yl]methyl-1H-imidazole-5-carboxylate and methyl 2-butyl-5-chloro-1-[3-bromo-2-(2-ethoxycarbonylphenyl)-2H-indazol-5-yl]methyl-1H-imidazole-4-carboxylate 2-[3-Bromo-5-(bromomethyl)-2H-indazol-2-yl]benzoate (0.356 g, 0.813 mmol) as obtained in Reference Example 5 was dissolved in N,N-dimethylformamide (4 ml). To the mixture were added methyl 2-butyl-4-chloro-1H-imidazole-5-carboxylate (0.159 g, 0.732 mmol) and potassium carbonate (0.112 g, 0.813 mmol), and the mixture was stirred at room temperature for one day and one night. The mixture was filtered, and the cake was washed twice with chloroform (5 ml). The N,N-dimethylformamide was evaporated from the filtrate, and the resultant mixture was subjected to flash chromatography on silica gel using a mixed solvent of hexane/ethyl acetate (3:1–1:1), whereby 0.148 g of methyl 2-butyl-4-chloro-1-[3-bromo-2-(2-ethoxycarbonylphenyl)-2H-indazol-5-yl]methyl-1H-imidazole-5-carboxylate and 26 mg of methyl 2-butyl-5-chloro-1-[3-bromo-2-(2-ethoxycarbonylphenyl)-2H-indazol-5-yl]methyl-1H-imidazole-4-carboxylate were obtained.

NMR (270 MHz, CDCl$_3$) methyl 2-butyl-4-chloro-1-[3-bromo-2-(2-ethoxycarbonylphenyl)-2H-indazol-5-yl]methyl-1H-imidazole-5-carboxylate: δ 8.1 (d, J=8 Hz, 1H); 7.0–7.7 (m, 6H); 5.6 (s, 1H); 4.0 (q, J=7 Hz, 2H); 3.8 (s, 3H); 2.7 (m, 2H); 1.7 (m, 2H); 1.4 (m, 2H ); 0.9 (t, J=7 Hz, 3H ); 0.8 (t, J=7 Hz, 3H )

methyl 2-butyl-5-chloro-1-[3-bromo-2-(2-ethoxycarbonylphenyl)-2H-indazol-5-yl]methyl-1H-imidazole-4-carboxylate: δ 8.1 (d, J=8 Hz, 1H); 7.0–7.7 (m, 6H); 5.3 (s, 1H); 4.0 (q, J=7 Hz, 2H); 3.9 (s, 3H); 2.7 (m, 2H); 1.7 (m, 2H); 1.4 (m, 2H); 0.9 (t, J=7 Hz, 3H ); 0.8 (t, J=7 Hz, 3H )

Example 9

Synthesis of disodium 1-[3-bromo-2-(2-carboxyphenyl)-2H-indazol-5-yl]methyl-2-butyl-4-chloro-1H-imidazole-5-carboxylate Ethanol (5.5 ml) and 1N aqueous sodium hydroxide (1.38 ml) were added to methyl 2-butyl-4-chloro-1-[3-bromo-2-(2-ethoxycarbonylphenyl)-2H-indazol-5-yl]methyl-1H-imidazole-5-carboxylate (0.132 g, 0.230 mmol) as obtained in Example 8, and the mixture was stirred at room temperature for one day. The mixture was concentrated in an evaporator, and ion-exchanged water (5 ml) was added thereto, followed by stirring. Conc. hydrochloric acid was dropwise added thereto to adjust its pH to 5–6. The resultant solid was filtered off and washed three times with ion-exchanged water (2.5 ml). Two equivalent amounts of N/10 aqueous sodium hydroxide was added to dissolve the solid obtained by drying in vacuo at 37° C. for two days. Lyophilization of the solution afforded 0.104 g of disodium 1-[3-bromo-2-(2-carboxyphenyl)-2H-indazol-5-yl]methyl-2-butyl-4-chloro-1H-imidazole-5-carboxylate.
NMR (270 MHz, D$_2$O) δ 7.2–7.9 (m, 7H); 5.8 (s, 2H); 2.7 (m, 2H); 1.5 (m, 2H); 1.3 (m, 2H ); 0.8 (t, J=7 Hz, 3H )

Example 10

Synthesis of disodium 2-butyl-5-chloro-1-[3-bromo-2-(2-carboxyphenyl)-2H-indazol-5-yl]methyl-1H-imidazole-4-carboxylate Methyl 2-butyl-5-chloro-1-[3-bromo-2-(2-ethylcarbonylphenyl)-2H-indazol-5-yl]methyl-1H-imidazole-5-carboxylate (26 mg) as obtained in Example 8 was treated in the same manner as in Example 9 to give 21 mg of disodium 2-butyl-5-chloro-1-[3-bromo-2-(2-carboxyphenyl)-2H-indazol-5-yl]methyl-1H-imidazole-4-carboxylate.
NMR (270 MHz, D$_2$O) δ 7.3–7.9 (m, 7H); 5.4 (s, 2H); 2.7 (m, 2H); 1.4 (m, 2H); 1.2 (m, 2H); 0.8 (t, J=7 Hz, 3H)

Example 11

Synthesis of 1-{[3-bromo-2-[2-(2-(triphenylmethyl)-2H-tetrazol-5-yl)phenyl]-2H-indazol-5-yl]methyl}-2-butyl-4-chloro-1H-imidazole-5-carbaldehyde By reacting 5-{2-[3-bromo-5-(bromomethyl)-2H-indazol-2-yl]phenyl}-2-(triphenylmethyl)-2H-tetrazole (1.00 g, 1.48 mmol) as obtained in Reference Example 9 with 2-butyl-4-chloro-1H-imidazole-5-carbaldehyde (0.248 g, 1.33 mmol) in the same manner as in Example 8, 0.74 g of 1-{[3-bromo-2-[2-(2 -(triphenylmethyl)-2H-tetrazol-5-yl)phenyl]-2H-indazol-5-yl]methyl}-2-butyl-4-chloro-1H-imidazole-5-carbaldehyde was obtained.
NMR (270 MHz, CDCl$_3$) δ 9.7 (s, 1H}; 8.4 (d, J=8 Hz, 1H); 6.8–7.7 (m, 21H); 5.6 (s, 2H); 2.6 (m, 2H); 1.6 (m, 2H); 1.4 (m, 2H); 0.9 (t, J=7 Hz, 3H)

Example 12

Synthesis of 1-{[3-bromo-2-[2-(1H-tetrazol-5-yl)phenyl]-2H-indazol-5-yl]methyl}-2-butyl-4-chloro-1H-imidazole-5-carbaldehyde Methanol (2 ml) was added to 1-{[3-bromo-2-[2-(2-(triphenylmethyl)-2H-tetrazol-5-yl)phenyl]-2H-indazol-5-yl]methyl}-2-butyl-4-chloro-1H-imidazole-5-carbaldehyde (0.200 g, 0.256 mmol) as obtained in Example 11, and the mixture was stirred at 10°C. Thereto was added 2N hydrochloric acid (0.23 ml), and the mixture was stirred at room temperature for 2 hours. Then, 2N hydrochloric acid (0.23 ml) and methanol (2.5 ml) were added thereto, and the mixture was stirred for 3 hours, after which conc. hydrochloric acid (2 ml) was added thereto and the mixture was stirred for 15.5 hours. 10N Aqueous sodium hydroxide was added to adjust its pH to 13, and the methanol was distilled away in an evaporator. The resultant solid was filtered, and the cake was washed twice with 1N sodium hydroxide (2.5 ml). The filtrate was washed with ether (5 ml), and conc. hydrochloric acid was dropwise added while stirring so as to adjust its pH to 4–5. The resultant solid was filtered off and washed twice with ion-exchanged water (5 ml). Drying in vacuo at 37° C. gave 45 mg of 1-{[3-bromo-2-[2-(1H-tetrazol-5-yl)phenyl]-2H-indazol-5-yl]methyl}-2-butyl-4-chloro-1H-imidazole-5-carbaldehyde.
NMR (270 MHz, Acetone-d$_6$) δ 9.8 (s, 1H); 8.3 (m, 1H); 7.2–7.9 (m, 6H); 5.8 (s, 2H); 2.3 (m, 2H); 1.7 (m, 2H); 1.4 (m, 2H); 0.9 (t, J=7 Hz, 3H)

Example 13

Synthesis of 1-{[3-bromo-2-[2- (2-(triphenylmethyl)-2H-tetrazol-5-yl)phenyl]-2H-indazol-5-yl]methyl}-2-butyl-4-chloro-5-(hydroxymethyl)-1H-imidazole 1-{[3-Bromo-2-[2-(2-(triphenylmethyl)-2H-tetrazol-5-yl)-phenyl)-2H-indazol-5-yl]methyl}-2-butyl-4-chloro-1H-imidazole-5-carbaldehyde (0.54 g, 0.690 mmol) as obtained in Example 11 was dissolved in tetrahydrofuran (7 ml), and the mixture was stirred. Thereto was added sodium borohydride (26 mg, 0.690 mmol), and the mixture was allowed to react at room temperature for 5 minutes. The mixture was concentrated in an evaporator, and partitioned by a saturated aqueous solution of sodium hydrogencarbonate (5 ml) and dichloromethane (5 ml). The organic layer was separated, and the water layer was extracted with dichloromethane (5 ml). The organic layers were combined, dried over magnesium sulfate, and then filtered. The solvent was evaporated in vacuo, and the mixture was subjected to flash chromatography on silica gel using a mixed solvent of dichloromethane/methanol, whereby 0.44 g of 1-{[3-bromo-2-[2-(2-(triphenylmethyl)-2H-tetrazol-5-yl)phenyl]-2H-indazol-5 -yl]methyl}-2-butyl-4-chloro-5-(hydroxymethyl)-1H-imidazole was obtained.
NMR (270 MHz, CDCl$_3$) δ 8.4 (d, J=8 Hz, 1H); 6.7–7.7 (m, 21H); 5.2 (s, 2H ); 4.3 (d, J=6 Hz, 2H); 2.6 (m, 2H); 1.7 (m, 2H); 1.3 (m, 2H); 0.9 (t, J=7 Hz, 3H)

Example 14

Synthesis of 1-{[3-bromo-2-[2-(1H-tetrazol-5-yl)phenyl]-2H-indazol -5-yl]methyl}-2-butyl-4-chloro-5-(hydroxymethyl)-1H-imidazole To 1-{[3-bromo-2-[2-(2-(triphenylmethyl)-2H-tetrazol-5-yl)phenyl]-2H-indazol-5-yl]methyl}-2-butyl-4-chloro-5-(hydroxymethyl)-1H-imidazole (obtained in Example 13) in dichloromethane (8.4 ml ) was dropwise added 14.7% hydrogen chloride in ethanol (5.6 ml), and the mixture was stirred at room temperature for 17 hours. The mixture was concentrated in an evaporator, and thereto were added water (5 ml), 10N aqueous sodium hydroxide (1.25 ml), and 1N aqueous sodium hydroxide (5 ml), followed by filtration. The cake was washed twice with water (5 ml), and conc. hydrochloric acid was dropwise added to the filtrate while stirring so as to adjust its pH to 4–5. The resultant solid was filtered off, washed twice with ion-exchanged water (2 ml), and dried in vacuo at 37° C. to give 11 mg of 1-{[3-bromo-2-[2-(1H-tetrazol-5-yl)phenyl]-2H-indazol-5-yl]methyl}-2-butyl-4-chloro-5-(hydroxymethyl)-1H-imidazole.
NMR (270 MHz, Acetone-d$_6$) δ 8.3 (m, 1H); 7.2–7.9 (m, 6H); 5.5 (s, 2H); 4.6 (s, 2H); 2.7 (m, 2H); 1.7 (m, 2H); 1.4 (m, 2H); 0.9 (t, J=7 Hz, 3H)

Example 15

Synthesis of 2-butyl-3-[3-bromo-2-(2-ethoxycarbonylphenyl)-2H-indazol-5-yl]methyl-3H-imidazo[4,5-b]pyridine Carbon tetrachloride (4 ml) was added to ethyl 2-(3-bromo-5-methyl-2H-indazol-2-yl)benzoate (0.300 g, 0.835 mmol) as obtained in Reference Example 4, and the mixture was stirred. Thereto were added N-bromosuccinimide (0.149 g, 0.835 mmol) and azobisisobutyronitrile (14 mg, 0.0835 mmol), and the mixture was refluxed under heating for 3.5 hours. After cooling, the mixture was filtered, and the cake was washed with carbon tetrachloride (1 ml) and the filtrate was concentrated. The residue was then dissolved in DMF (dimethylformamide, 1 ml) and added to a solution obtained by adding sodium hydride (27 mg, 0.668 mmol) to 2-butyl-1H-imidazo[4,5-b]pyridine (0.117 g, 0.668 mmol) in DMF (2 ml) and stirring the solution for 30 minutes. The mixture was stirred at room temperature for 30 minutes, concentrated, and partitioned by ethyl acetate (5 ml) and water (5 ml). The organic layer was washed twice with water (5 ml), dried over magnesium sulfate, and then filtered. The filtrate was concentrated and subjected to flash chromatography on silica gel using a mixed solvent of hexane/ethyl acetate (1:2), whereby 0.144 g of 2-butyl-3-[3-bromo-2-(2-ethoxycarbonylphenyl)-2H-indazol-5-yl]methyl-3H-imidazo[4,5-b]pyridine was obtained.

NMR (270 MHz, CDCl$_3$) δ 7.21–8.38 (m, 10H); 5.60 (s, 2H); 3.98 (q, J=7 Hz, 2H); 2.87 (t, J=7.8 Hz, 2H); 1.84 (m, 2H); 1.44 (m, 2H); 0.90 (t, J=7.6 Hz, 3H); 0.76 (t, J=7.0 Hz, 3H)

Example 16

Synthesis of 2-butyl-3-[3-bromo-2-(2-carboxyphenyl)-2H-indazol-5-yl]methyl-3H-imidazo[4,5-b]pyridine sodium salt Ethanol (1.3 ml) and 1N aqueous sodium hydroxide (0.275 ml) were added to 2-butyl-3-[3-bromo-2-(2-ethoxycarbonylphenyl)-2H-indazol-5-yl]methyl-3H-imidazo[4,5-b]pyridine (0.144 g, 0.270 mmol) as obtained in Example 15, and the mixture was stirred at room temperature for 16.5 hours, followed by 3.5 hours of reflux under heating. After cooling, sodium hydroxide (24 mg) was added thereto, and the mixture was stirred at room temperature for 1 hour. After concentration, the mixture was partitioned by water (2.5 ml) and ether (5 ml). Conc. hydrochloric acid was dropwise added to the water layer while stirring so as to adjust its pH to 5. The resultant solid was filtered off, washed twice with water (1 ml), and dried. Thereto were added water and an equivalent amount of 1N aqueous sodium hydroxide, and the water was distilled away by centrifugal evaporator overnight. The obtained solid was dried in vacuo overnight at 37° C. to give 89 mg of 2-butyl-3-[3-bromo-2-(2-carboxyphenyl)-2H-indazol-5-yl]methyl-3H-imidazo[4,5-b]pyridine sodium salt.

NMR (270 MHz, D$_2$O) δ 7.14–8.24 (m, 10H); 5.47 (s, 2H); 2.82 (t, J=8 Hz, 2H); 1.56 (m, 2H); 1.24 (m, 2H); 0.73 (t, J=7.3 Hz, 3H)

Example 17

Synthesis of 3-[3-bromo-2-(2-ethoxycarbonylphenyl)-2H-indazol-5-yl]methyl-5,7-dimethyl-2-ethyl-3H-imidazo[4,5-b]pyridine Carbon tetrachloride (2 ml) was added to ethyl 2-(3-bromo-5-methyl-2H-indazol-2-yl)benzoate (0.450 g, 1.25 mmol) as obtained in Reference Example 4, and the mixture was stirred. Thereto were added N-bromosuccinimide (0.223 g, 1.25 mmol) and azobisisobutyronitrile (21 mg, 0.125 mmol), and the mixture was refluxed under heating for 3.5 hours. After cooling, it was filtered, and the cake was washed with dichloromethane (2 ml) and the filtrate was concentrated. The residue was then dissolved in DMF (2 ml), and added to a solution obtained by adding sodium hydride (40 mg, 1.00 mmol) to 2-ethyl-5,7-dimethyl-1H-imidazo[4,5-b]pyridine (0.176 mg, 1.00 mmol) in DMF (4 ml) and stirring the solution for 30 minutes. The mixture was stirred at room temperature for 30 minutes, concentrated, and partitioned by ethyl acetate (10 ml) and water (10 ml). The organic layer was dried over magnesium sulfate, and then filtered. The filtrate was concentrated and subjected to flash chromatography on silica gel using a mixed solvent of hexane/ethyl acetate (2:3), whereby 0.176 g of 3-[3-bromo-2-(2-ethoxycarbonylphenyl)-2H-indazol-5-yl]methyl-5,7-dimethyl-2-ethyl-3H-imidazo[4,5-b]pyridine was obtained.

NMR (270 MHz, CDCl$_3$) δ 7.18–8.15 (m, 7H); 6.92 (s, 1H); 5.55 (s, 2H); 3.98 (q, J=7.3 Hz, 2H); 2.84 (q, J=7.6 Hz, 2H); 2.65 (s, 3H); 2.62 (s, 3H); 1.35 (t, J=7.8 Hz, 3H); 0.74 (t, J=7.3 Hz, 3H)

Example 18

Synthesis of sodium 3-[3-bromo-2-(2-carboxyphenyl)-2H-indazol-5-yl]methyl-5,7-dimethyl-2-ethyl-3H-imidazo[4,5-b]pyridine Ethanol (1.3 ml), water (0.33 ml), and sodium hydroxide (39 mg, 0.986 mmol). were added to 3-[3-bromo-2-(2-ethoxycarbonylphenyl)-2H-indazol-5-yl]methyl-5,7-dimethyl-2-ethyl-3H-imidazo[4,5-b]pyridine (0.175 mg, 0.329 mmol) as obtained in Example 17, and the mixture was stirred at room temperature for 19 hours. After concentration, it was partitioned by water (2.5 ml ) and ether (5 ml ). Conc. hydrochloric acid was dropwise added to the water layer while stirring so as to adjust its pH to 5. The resultant solid was filtered off, washed twice with water (1 ml), and dried. Thereto were added water and an equivalent amount of 1N aqueous sodium hydroxide.

Lyophilization of the mixture afforded 106 mg of sodium 3-[3-bromo-2-(2-carboxyphenyl)-2H-indazol-5-yl]methyl-5, 7-dimethyl-2-ethyl-3H-imidazo[4,5-b]pyridine.

NMR (270 MHz, D$_2$O) δ 7.18–7.81 (m, 7H); 6.96 (s, 1H); 5.54(s, 2H); 2.89 (q, J=7.6 Hz, 2H); 2.53 (s, 3H); 2.49 (s, 3H); 1.26 (t, J=7.6 Hz, 3H )

Example 19

Synthesis of 3-[3-bromo-2-(2-ethoxycarbonylphenyl)-2H-indazol-5-yl]methyl-7-methyl-2-propyl-3H-imidazo[4,5-b]pyridine Carbon tetrachloride (4 ml) was added to ethyl 2-(3-bromo-5-methyl-2H-indazol-2-yl)benzoate (0.300 g, 0.835 mmol) as obtained in Reference Example 4, and the mixture was stirred. Thereto were added N-bromosuccinimide (0.149 g, 0.835 mmol) and azobisisobutyronitrile (14 mg, 0.0835 mmol), and the mixture was refluxed under heating for 3.5 hours. After cooling, it was filtered, and the cake was washed twice with dichloromethane (2.5 ml) and the filtrate was concentrated. The residue was then dissolved in DMF (1 ml) and added to a solution obtained by adding sodium hydride (27 mg, 0.668 mmol) to 7-methyl-2-propyl-1H-imidazo[4,5-b]pyridine (0.117 g, 0.668 mmol) in DMF (2 ml) and stirring the solution for 30 minutes. The mixture was stirred at room temperature for 30 minutes, concentrated, and partitioned by ethyl acetate (5 ml) and water (5 ml). The organic layer was washed twice with water (5 ml), dried over magnesium sulfate, and then filtered. The filtrate was concentrated and subjected to flash chromatography on silica gel using a mixed solvent of hexane/ethyl acetate (2:3), whereby 70 mg of 3-[3-bromo-2-(2-ethoxycarbonylphenyl)-2H-indazol-5-yl]methyl-7-methyl-2-propyl-3H-imidazo[4,5-b]pyridine was obtained.

NMR (270 MHz, CDCl$_3$) δ 7.04–8.25 (m, 9H); 5.59 (s, 2H); 3.98 (q, J=7.0 Hz, 2H); 2.85 (t, J=7.8 Hz, 2H); 2.71 (s, 3H); 1.81 (m, 2H); 1.01 (t, J=7.8 Hz, 3H); 0.74 (t, J=7.0 Hz,

Example 20

Synthesis of 3-[3-bromo-2-(2-carboxyphenyl)-2H-indazol-5-yl]-methyl-7-methyl-2-propyl-3H-imidazo[4,5-b]pyridine Ethanol (1.2 ml), water (0.3 ml), and sodium hydroxide (34 mg, 0.840 mmol) were added to 3-[3-bromo-2-(2-ethoxycarbonylphenyl)-2H-indazol-5-yl]methyl-7-methyl-2-propyl-3H-imidazo[4,5-b]pyridine (0.149 mg, 0.280 mmol) obtained from two batches of Example 19, and the mixture was stirred at room temperature for 15.5 hours. After concentration, it was partitioned by water (2.5 ml) and ether (5 ml). Conc. hydrochloric acid was dropwise added to the water layer while stirring so as to adjust its pH to 5. The resultant solid was filtered off, washed twice with water (1 ml), and dried overnight at 37° C. to give 84 mg of 3-[3-bromo-2-(2-carboxyphenyl)-2H-indazol-5-yl]methyl-7-methyl-2-propyl-3H-imidazo[4,5-b]pyridine.
NMR (270 MHz, DMSO-d$_6$) δ 12.9 (bs, 1H); 7.11–8.22 (m, 9H); 5.62 (s, 2H); 2.90 (t, J=7.3 Hz, 2H); 2.57 (s, 3H); 1.73 (m, 2H); 0.93 (t, J=7.3 Hz, 3H)

Reference Example 10

Synthesis of 3-{[3-bromo-2-[2-(2-(triphenylmethyl)-2H-tetrazol-5-yl)phenyl]-2H-indazol-5-yl]methyl}-2-ethyl-5,7-dimethyl-3H-imidazo[4,5-b]pyridine To a solution obtained by adding sodium hydride (15 mg, 0.366 mmol) to 2-ethyl-5,7-dimethyl-1H-imidazo[4,5-b]pyridine (58 mg, 0.333 mmol) in DMF (2 ml) and stirring for 30 minutes was added 5-[2-(3-bromo-5-(bromomethyl)-2H-indazol-2-yl)phenyl]-2-(triphenylmethyl)-2H-tetrazol (0.250 g, 0.370 mmol) as obtained in Reference Example 9. The mixture was stirred at room temperature for 16 hours. After concentration, it was partitioned by ethyl acetate (10 ml) and water (5 ml). The organic layer was dried over magnesium sulfate, and filtered. The filtrate was concentrated, and subjected to flash chromatography on silica gel using a mixed solvent of dichloromethane/methanol (100:1), whereby 0.134 g of 3-{[3-bromo-2-[2-(2-(triphenylmethyl)-2H-tetrazol-5-yl)phenyl]-2H-indazol-5-yl]methyl}-2-ethyl-5,7-dimethyl-3H-imidazo[4,5-b]pyridine was obtained.
NMRR (270 MHz, CDCl$_3$) δ 8.43 (d, J=7.3 Hz, 1H); 6.74–7.70 (m, 22H); 5.46 (s, 2H); 2.72 (q, J=7.8 Hz, 3H); 2.67 (s, 3H); 2.60 (s, 3H); 1.29 (t, J=7.6 Hz, 3H)

Example 21

Synthesis of 3-{[3-bromo-2-[2-(1H-tetrazol-5-yl)phenyl]-2H-indazol-5-yl]methyl}-2-ethyl-5,7-dimethyl-3H-imidazo[4,5-b]pyridine 3-{[3-Bromo-2-[2-(2-(triphenylmethyl)-2H-tetrazol-5-yl)-phenyl]-2H-indazol-5-yl]methyl}-2-ethyl-5,7-dimethyl-3H-imidazo[4,5-b]pyridine (0.134 g) as obtained in Reference Example 10 was dissolved in dichloromethane (2 ml), and thereto was added formic acid (2 ml). The mixture was stirred at room temperature for 48 hours, and concentrated. Thereto was added 1N aqueous sodium hydroxide to adjust the pH to 12. The liquid portion was taken and washed with ether (10 ml) and dichloromethane (20 ml). Conc. hydrochloric acid was added to the water layer while stirring to adjust the pH to 7, and the water layer was extracted with ethyl acetate (20 ml). The organic layer was dried over magnesium sulfate, filtered, and concentrated. Acetone (1 ml) was added to the residue for dissolution, and hexane (15 ml) was added. The resultant solid was filtered off, washed twice with hexane (2.5 ml), and dried in vacuo to give 7.0 mg of 3-{[3-bromo-2-[2-(1H-tetrazol-5-yl)-phenyl]-2H-indazol-5-yl]methyl})-2-ethyl-5, 7-dimethyl-3 H-imidazo[4,5-b]pyridine.
NMR (270 MHz, Acetone-d$_6$) δ 7.37–8.34 (m, 7H); 7.02 (s, 1H); 5.69 (s, 2H); 2.97 (q, J=7.3 Hz, 2H ); 2.63 (s, 3H ); 2.61 (s, 3H ); 1.39 (t, J=7.8 Hz, 3H)

Reference Example 11

Synthesis of 3-{[3-bromo-2-[2-(2-(triphenylmethyl)-2H-tetrazol-5-yl)phenyl]-2H-indazol-5-yl]methyl})-7-methyl-2-propyl-3H-imidazo[4,5-b]pyridine The procedure similar to that in Reference Example 10 using 7-methyl-2-propyl-1H-imidazo[4,5-b]pyridine (0.22 g, 0.325 mmol) in place of 2-ethyl-5,7-dimethyl-1H-imidazo[4,5-b]pyridine afforded 82 mg of 3-{[3-bromo-2-[2-(2-(triphenylmethyl)-2H-tetrazol-5-yl)phenyl]-2H-indazol-5-yl]methyl}-7-methyl-2-propyl-3H-imidazo[4,5-b]pyridine.
NMR (270 MHz, CDCl$_3$) δ 8.4 (d, J=7 Hz, 1H ); 8.2 (d, J=5 Hz, 1H ); 6.7–7.7 (m, 22H); 5.5 (s, 2H); 2.8 (m, 2H); 2.7 (s, 3H); 1.8 (m, 2H); 1.0 (t, J=7 Hz, 3H)

Example 22

Synthesis of 3-{[3-bromo-2-[2-(1H-tetrazol-5-yl)phenyl]-2H-indazol-5-yl]methyl}-7-methyl-2-propyl-3H-imidazo[4,5-b]pyridine By treating 3-{[3-bromo-2-[2-(2-triphenylmethyl)-2H-tetrazol-5-yl]phenyl]-2H-indazol-5-yl]methyl}-7-methyl-2-propyl-3H-imidazo[4,5-b]pyridine (82 mg) as obtained in Reference Example 11 in the same manner as in Example 21, 10 mg of 3-{[3-bromo-2-[2-(1H-tetrazol-5-yl)phenyl]-2H-indazol-5-yl]methyl}-7-methyl-2-propyl-3H-imidazo[4,5-b]pyridine was obtained.
NMR (270 MHz, Acetone-d$_6$) δ 6.9–8.1 (m, 9H); 5.5 (s, 2H); 2.8 (m, 2H); 2.5 (s, 3H); 1.7 (m, 2H); 0.9 (t, J=7 Hz, 3H).

Reference Example 12

Synthesis of 3-{[3-bromo-2-[2-(2-(triphenylmethyl)-2H-tetrazol-5-yl)phenyl]-2H-indazol-5-yl]methyl}-2-butyl-3H-imidazo[4,5-b]pyridine The procedure similar to that in Reference Example 10 using 2-butyl-1H-imidazo[4,5-b]pyridine (0.22 g, 0.325 mmol) in place of 2-ethyl-5,7-dimethyl-1H-imidazo[4,5-b]pyridine afforded 75 mg of 3-{[3-bromo-2-[2-(2-(triphenylmethyl)-2H-tetrazol-5-yl)-phenyl]-2H-indazol-5-yl]methyl}-2-butyl-3H-imidazo[4,5-b]pyridine.
NMR (270 MHz, CDCl$_3$) δ 8.4 (m, 2H); 8.1 (d, J=6 Hz, 1H); 6.7–7.7 (m, 22H); 5.5 (s, 2H); 2.8 (m, 2H); 1.8 (m, 2H); 1.4 (m, 2H); 0.9 (t, J=7 Hz, 3H)

Example 23

Synthesis of 3-{[3-bromo-2-[2-(1H-tetrazol-5-yl)phenyl]-2H-indazol-5-yl]methyl}-2-butyl-3H-imidazo[4,5-b]pyridine By treating 3-{[3-bromo-2-[2-(2-(triphenylmethyl)-2H-tetrazol-5-yl)phenyl]-2H-indazol-5-yl]methyl}-2-butyl-3H-imidazo[4,5-b]pyridine (75 mg) as obtained in Reference Example 12 in the same manner as in Example 21, 9 mg of 3-{[3-bromo-2-[2-(1H-tetrazol-5-yl)phenyl]-2H-indazol-5-yl]methyl}-2-butyl-3H-imidazo[4,5-b]pyridine was obtained.

Reference Example 13

Synthesis of 5-[2-(3-chloro-5-methyl-2H-indazol-2-yl)phenyl]-2-(triphenylmethyl)-2H-tetrazole By treating 5-[2-(5-methyl-2H-indazol-2-yl)phenyl]-2-(triphenylmethyl)-2H-tetrazole as obtained in Reference Example 8, in the same manner as in Reference Example 4 by using N-chlorosuccinimide (1 equivalent amount) in place of N-bromosuccinimide, 5-[2-(3-chloro-5-methyl-2H-indazol-2-yl)-phenyl]-2-(triphenylmethyl)-2H-tetrazole was obtained.

NMR (270 MHz, CDCl$_3$) δ 8.4 (d, J=7 Hz, 1H); 6.7–7.7 (m, 21H); 2.4 (s, 3H)

Reference Example 14

Synthesis of 3-{[3-chloro-2-[2-(2-(triphenylmethyl)-2H-tetrazol-5-yl)phenyl]-2H-indazol-5-yl]methyl}-2-ethyl-5,7-dimethyl-3H-imidazo[4,5-b]pyridine The procedure similar to that in Example 17 using 5-[2-(3-chloro-5-methyl-2H-indazol-2-yl)phenyl]-2-(triphenylmethyl)-2H-tetrazole as obtained in Reference Example 13 in place of 5-[2-(3-bromo-5-methyl-2H-indazol-2-yl)phenyl]-2-(triphenylmethyl)-2H-tetrazole afforded 0.492 g of 3-{[3-chloro-2-[2-(2-(triphenylmethyl)-2H-tetrazol-5-yl)phenyl]-2H-indazol-5-yl]methyl}-2-ethyl-5,7-dimethyl-3H-imidazo[4,5-b]pyridine.

NMR (270 MHz, CDCl$_3$) δ 8.4 (d, J=7 Hz, 1H); 6.7–7.8 (m, 22H); 5.4 (s, 2H); 2.7 (q, J=8 Hz, 2H); 2.67 (s, 3H); 2.60 (s, 3H); 1.3 (t, J=8 Hz, 3H)

Example 24

Synthesis of 3-{[3-chloro-2-[2-(1H-tetrazol-5-yl)phenyl]-2H-indazol-5-yl]methyl}-2-ethyl-5, 7-dimethyl-3H-imidazo[4,5-b]pyridine To 3-{[3-chloro-2-[2-(2-(triphenylmethyl)-2H-tetrazol-5-yl)phenyl]-2H-indazol-5-yl]methyl}-2-ethyl-5,7-dimethyl-3H-imidazo[4,5-b]pyridine (0.492 g) as obtained in Reference Example 14 was added methanol (5.5 ml), and the mixture was stirred. Thereto was dropwise added conc. hydrochloric acid (5.5 ml) under ice-cooling. Then, the mixture was stirred at room temperature for 19 hours. 10N Aqueous sodium hydroxide was added under ice-cooling so as to adjust the pH to 13, followed by addition of ion-exchanged water (10 ml). The mixture was filtered, and the cake was washed with 1N aqueous sodium hydroxide (10 ml). Conc. hydrochloric acid was added to the filtrate while stirring so as to adjust the pH to 5, and the filtrate was extracted with ethyl acetate (55 ml). The organic layer was dried over magnesium sulfate, filtered, and concentrated. The residue was dissolved in ethyl acetate (1 ml ), and hexane (15 ml ) was added while stirring. The resultant solid was filtered off, washed twice with hexane (5 ml ), and dried in vacuo to give 43 mg of 3-{[3-chloro-2-[2-(1H-tetrazol-5-yl)phenyl]-2H-indazol-5-yl]methyl}-2-ethyl-5,7-dimethyl-3H-imidazo[4,5-b]pyridine.

NMR (270 MHz, CDCl$_3$) δ 8.5 (m, 1H); 7.2–7.8 (m, 6H); 6.9 (s, 1H); 5.5 (s, 2H); 2.8 (q, J=7 Hz, 2H); 2.61 (s, 3H); 2.58 (s, 3H); 1.3 (t, J=7 Hz, 3H)

Reference Example 15

Synthesis of 3-chloro-2-(5-methyl-2H-indazol-2-yl)benzonitrile

To 5-methyl-2-nitrobenzaldehyde (10.9 g, 66.0 mmol) as obtained in Reference Example 1 was added toluene (66 ml), and the mixture was stirred. Thereto was added 2-amino-6-chlorobenzonitrile (10.1 g, 66.0 mmol). After refluxing under stirring for one day, molecular seives 5A (66 g) was added thereto and the mixture was left standing overnight. The mixture was filtered, and the cake was washed 6 times with chloroform (70 ml). The washing solution was concentrated and suspended in hexane (70 ml). The resultant solid was filtered off, washed with hexane (70 ml) and hexane (35 ml), and dried in vacuo. Triethyl phosphite (36.5 ml, 212.7 mmol) was added to the residue, and the mixture was refluxed for an hour, followed by cooling. The resultant solid was filtered off, washed 4 times with methanol (30 ml), and dried in vacuo to give 4.87 g of 3-chloro-2-(5-methyl-2H-indazol-2-yl)-benzonitrile. The secondary crystals (0.19 g) were further obtained from the washing solution.

NMR (270 MHz, CDCl$_3$) δ 8.5 (s, 1H); 7.2–7.9 (m, 6H); 2.4 (s, 3H)

Reference Example 16

Synthesis of 5-[3-chloro-2-(5-methyl-2H-indazol-2-yl)phenyl]-2-(triphenylmethyl)-2H-tetrazole The procedure similar to that in Reference Example 8 using 3-chloro-2-(5-methyl-2H-indazol-2-yl)benzonitrile (5.06 g) as obtained in Reference Example 15 in place of 2-(5-methyl-2H-indazol-2-yl)benzonitrile afforded 8.71 g of 5-[3-chloro-2-(5 -methyl-2H-indazol-2-yl)phenyl]-2-(triphenylmethyl)-2H-tetrazole.

NMR (270 MHz, CDCl$_3$) δ 6.8–7.9 (m, 22H); 2.4 (s, 3H)

Reference Example 17

Synthesis of 3-{[3-bromo-2-[3-chloro-2-(2-(triphenylmethyl)-2H-tetrazol-5-yl)phenyl]-2H-indazol-5-yl]methyl}-2-ethyl-5,7-dimethyl-3H-imidazo[4,5-b]pyridine Carbon tetrachloride (40 ml) was added to 5-[3-chloro-2-[5-methyl-2H-indazol-2-yl)phenyl]-2-(triphenylmethyl)-2H-tetrazole (4.0 g, 7.23 mmol) as obtained in Reference Example 16, and the mixture was stirred. Thereto were added N-bromosuccinimide (1.42 g, 7.96 mmol), and the mixture was refluxed under heating for an hour. Thereto were added N-bromosuccinimide (1.22 g, 6.89 mmol) and azobisisobutyronitrile (57 mg, 0.345 mmol), and the mixture was refluxed under heating for 2.5 hours. After cooling, the mixture was diluted with dichloromethane (40 ml), and poured into water (40 ml). The organic layer was dried over magnesium sulfate, filtered, and concentrated. The residue was dried in vacuo. The residue thus obtained was added to a solution obtained by adding, in a different reaction vessel, sodium hydride (0.257 g, 5.88 mmol) to 2-ethyl-5,7-dimethyl-1H-imidazo[4,5-b]pyridine (1.03 g, 5.88 mmol) in DMF (39 ml) and stirring the solution for 30 minutes. The mixture was stirred at room temperature for 15 hours, concentrated, and partitioned by ethyl acetate (100 ml) and water (100 ml). The water layer was extracted with ethyl acetate (100 ml) and then with dichloromethane (100 ml). The organic layer was dried over magnesium sulfate, and then filtered. The filtrate was concentrated and subjected to flash chromatography on silica gel using a mixed solvent of hexane/ethyl acetate (2:3), whereby 0.992 g of 3-{[3-bromo-2-[3-chloro-2-(2-(triphenylmethyl)-2H-tetrazol-5-yl)phenyl]-2H-indazol-5-yl]methyl}-2-ethyl-5, 7-dimethyl-3H-imidazo[4,5-b]pyridine was obtained.

NMR (270 MHz, CDCl$_3$) δ 6.8–7.7 (m, 22H); 5.5 (s, 2H); 2.7 (q, J=8 Hz, 3H);2.67 (s, 3H);2.59 (s, 3H); 1.3 (t, J=8 Hz, 3H)

Example 25

Synthesis of 3-{[3-bromo-2-[3-chloro-2-(1H-tetrazol-5-yl)-phenyl]-2H-indazol-5-yl]methyl}-2-ethyl-5,7-dimethyl-3H-imidazo[4,5-b]pyridine 3-{[3-Bromo-2-[3-chloro-2-(2-(triphenylmethyl)-2H-tetrazol-5-yl)phenyl]-2H-indazol-5-yl]methyl}-2-ethyl-5,7-dimethyl-3H-imidazo[4,5-b]pyridine (0.800 g, 0.994 mmol) as obtained in Reference Example 17 was treated in the same manner as in Example 24 to give 0.324 g of 3-{[3-bromo-2-[3-chloro-2-(1H-tetrazol-5-yl)phenyl]-2H-indazol-5-yl]methyl}-2-ethyl-5, 7-dimethyl -3H-imidazo[4, 5-b]pyridine.

NMR (270 MHz, CDCl$_3$) δ 6.9–7.6 (m, 6H); 6.8 (s, 1H); 5.4 (s, 2H); 2.7 (q, J=7 Hz, 2H); 2.51 (s, 3H); 2.48 (s, 3H); 1.1 (t, J=7 Hz, 3H)

In a similar manner, the following compounds can be obtained.

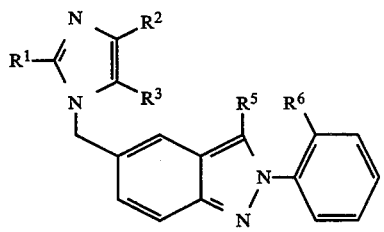

| R$^1$ | R$^2$ | R$^3$ | R$^5$ | R$^6$ |
|---|---|---|---|---|
| n-C$_4$H$_9$ | Cl | CH$_2$OH | H | tetrazolyl |
| " | " | " | Cl | COOH |
| " | " | " | " | COOC$_2$H$_5$ (Compound A) |
| " | " | " | " | tetrazolyl |
| " | " | COOH | H | COOH |
| " | " | " | " | tetrazolyl |
| " | " | " | Cl | COOH |
| " | " | " | " | tetrazolyl |
| " | " | " | Br | COOH (Compound B) |
| " | " | " | " | tetrazolyl |
| n-C$_5$H$_{11}$ | Cl | CH$_2$OH | H | COOH |
| " | " | " | " | tetrazolyl |
| " | " | " | Cl | COOH |
| " | " | " | " | tetrazolyl |
| " | " | " | Br | COOH |
| " | " | " | " | tetrazolyl (Compound C) |
| " | " | COOH | H | COOH |
| " | " | " | " | tetrazolyl |
| " | " | " | Cl | COOH |
| " | " | " | " | tetrazolyl |
| " | " | " | Br | COOH (Compound D) |
| " | " | " | " | tetrazolyl |
| n-C$_4$H$_9$ | Cl | CHO | H | tetrazolyl |
| " | " | " | Cl | COOH (Compound E) |
| " | " | " | " | tetrazolyl |

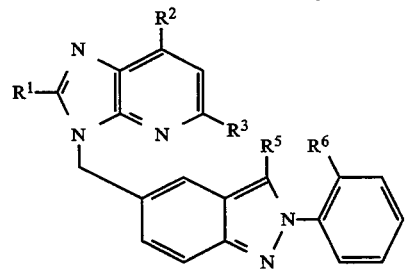

| R$^1$ | R$^2$ | R$^3$ | R$^5$ | R$^6$ |
|---|---|---|---|---|
| n-C$_4$H$_9$ | H | H | H | COOH |
| " | " | " | " | COOC$_2$H$_5$ |
| " | " | " | " | COOPh |
| " | " | " | " | NHSO$_2$CF$_3$ |
| " | " | " | " | tetrazolyl |
| " | " | " | Cl | COOH |
| " | " | " | " | COOC$_2$H$_5$ (Compound F) |
| " | " | " | " | COOPh |
| " | " | " | " | NHSO$_2$CF$_3$ |
| " | " | " | " | tetrazolyl |
| " | " | " | Br | COOPh |
| " | " | " | " | NHSO$_2$CF$_3$ |
| n-C$_3$H$_7$ | H | H | H | COOH |
| " | " | " | " | COOC$_2$H$_5$ |
| " | " | " | " | tetrazolyl |
| " | " | " | Cl | COOH |
| " | " | " | " | COOC$_2$H$_5$ |
| " | " | " | " | tetrazolyl |
| " | " | " | Br | COOH |
| " | " | " | " | COOC$_2$H$_5$ (Compound G) |
| " | " | " | " | tetrazolyl |
| O-n-C$_3$H$_7$ | H | H | H | COOH |
| " | " | " | " | COOC$_2$H$_5$ |
| " | " | " | " | tetrazolyl |
| " | " | " | Cl | COOH |
| " | " | " | " | COOC$_2$H$_5$ |
| " | " | " | " | tetrazolyl |
| " | " | " | Br | COOH (Compound H) |
| " | " | " | " | COOC$_2$H$_5$ |
| " | " | " | " | tetrazolyl |
| C$_2$H$_5$ | H | H | H | COOH |
| " | " | " | " | COOC$_2$H$_5$ |
| " | " | " | " | tetrazolyl |
| " | " | " | Cl | COOH |
| " | " | " | " | COOC$_2$H$_5$ |
| " | " | " | " | tetrazolyl |
| " | " | " | Br | COOH |
| " | " | " | " | COOC$_2$H$_5$ (Compound I) |
| " | " | " | " | tetrazolyl |
| OC$_2$H$_5$ | H | H | H | COOH |
| " | " | " | " | COOC$_2$H$_5$ |
| " | " | " | " | tetrazolyl |
| " | " | " | Cl | COOH |
| " | " | " | " | COOC$_2$H$_5$ |
| " | " | " | " | tetrazolyl |
| " | " | " | Br | COOH |
| " | " | " | " | COOC$_2$H$_5$ (Compound J) |
| " | " | " | " | tetrazolyl |
| n-C$_3$H$_7$ | CH$_3$ | H | H | COOH |
| " | " | " | " | COOC$_2$H$_5$ |
| " | " | " | " | tetrazolyl |
| " | " | " | Cl | COOH |
| " | " | " | " | COOC$_2$H$_5$ (Compound K) |
| " | " | " | " | tetrazolyl |
| OC$_2$H$_5$ | CH$_3$ | H | H | COOH |
| " | " | " | " | tetrazolyl |
| " | " | " | Cl | COOH |
| " | " | " | " | tetrazolyl |
| " | " | " | Br | COOH (Compound L) |
| " | " | " | " | tetrazolyl |
| C$_2$H$_5$ | CH$_3$ | CH$_3$ | H | COOH |
| " | " | " | " | COOC$_2$H$_5$ |
| " | " | " | " | tetrazolyl |
| " | " | " | Cl | COOH |
| " | " | " | " | COOC$_2$H$_5$ (Compound M) |
| " | " | " | " | tetrazolyl |
| OCH$_3$ | CH$_3$ | CH$_3$ | H | COOH |
| " | " | " | " | tetrazolyl |
| " | " | " | Cl | COOH |
| " | " | " | " | tetrazolyl |
| " | " | " | Br | COOH (Compound N) |
| " | " | " | " | tetrazolyl |
| CH$_3$ | CH$_3$ | CH$_3$ | H | COOH |
| " | " | " | " | tetrazolyl |
| " | " | " | Cl | COOH |
| " | " | " | " | tetrazolyl |
| " | " | " | Br | COOH (Compound O) |
| " | " | " | " | tetrazolyl |

Note: Ph stands for phenyl.

NMR
Compound A: CDCl$_3$
δ 7.0–8.3 (m, 7H); 5.4 (s, 2H); 4.6 (s, 2H); 4.0 (q, J=7.0 Hz, 2H); 2.9 (bs, 1H); 2.6 (t, J=7.0 Hz, 2H); 1.7 (m, 2H); 1.3 (m, 2H); 0.9 (t, J=7.0 Hz, 3H); 0.8 (t, J=7.0 Hz, 3H)
Compound B: DMSO-d$_6$ δ 12.91 (brs, 2H); 7.0–7.9 (m, 7H); 5.6f (s, 2H); 2.60 (t, J=7.0 Hz, 2H); 1.53 (m, 2H); 1.27 (m, 2H); 0.81 (t, J=7.0 Hz, 3H)

Compound C: DMSO-$d_6$

δ 7.0–7.9 (m, 7H); 5.24 (s, 2H); 5.20 (brs, 2H); 4.34 (s, 2H); 2.48 (t, J=7.0 Hz, 2H); 1.64–1.78 (m, 2H); 1.27–1.34 (m, 4H); 0.84 (t, J=7.0 Hz, 3H)

Compound D: DMSO-$d_6$

δ 12.97 (brs, 2H); 7.0–7.9 (m, 7H); 5.60 (s, 2H); 2.60 (t, J=7.0 Hz, 2H); 1.4–1.6 (m, 4H); 1.25 (m, 2H); 0.79 (t, J=7.0 Hz, 3H)

Compound E: CDCl$_3$

δ 9.75 (s, 1H); 7.1–8.1 (m, 7H); 5.70 (s, 2H); 2.76 (t, J=7.0 Hz, 2H); 1.68 (m, 2H); 1.37 (m, 2H); 0.81 (t, J=7.0 Hz, 3H)

Compound F: CDCl$_3$

δ 7.2–8.4 (m, 10H); 5.60 (s, 2H); 3.98 (q, J=7.3 Hz, 2H); 2.86 (m, 2H); 1.83 (m, 2H); 1.44 (m, 2H); 0.90 (t, J=7.8 Hz, 3H); 0.76 (t, J=7.3 Hz, 3H)

Compound G: CDCl$_3$

δ 7.2–8.4 (m, 10H); 5.55 (s, 2H); 3.98 (q, J=7.0 Hz, 2H); 2.89 (m, 2H); 1.81 (m, 2H); 1.00 (t, J=7.8 Hz, 3H); 0.74 (t, J=7.0 Hz, 3H)

Compound H-Na salt: DMSO-$d_6$

δ 7.14–8.00 (m, 10H); 5.60 (s, 2H); 4.48 (t, J=7.0 Hz, 2H); 1.77 (m, 2H); 0.93 (t, J=7.0 Hz, 3H)

Compound I: CDCl$_3$

δ 7.18–8.15 (m, 10H); 5.55 (s, 2H); 3.98 (q, J=7.3 Hz, 2H); 2.94 (q, J=7.7 Hz, 2H); 1.35 (t, J=7.7 Hz, 3H); 0.74 (t, J=7.3 Hz, 3H)

Compound J: CDCl$_3$

δ 7.1–8.2 (m, 10H); 5.50 (s, 2H); 4.60 (q, J=7.0 Hz, 2H); 3.98 (q, J=7.1 Hz, 2H); 1.44 (t, J=7.0 Hz, 3H); 0.74 (t, J=7.1 Hz, 3H)

Compound K: CDCl$_3$

δ 7.0–8.3 (m, 9H); 5.58 (s, 2H); 3.98 (q, J=7.0 Hz, 2H); 2.85 (m, 2H); 2.71 (s, 3H); 1.81 (m, 2H); 1.01 (t, J=7.8 Hz, 3H); 0.74 (t, J=7.0 Hz, 3H)

Compound L-Na salt: DMSO-$d_6$

δ 7.1–7.9 (m, 9H); 5.54 (s, 2H); 4.56 (q, J=7.0 Hz, 2H); 2.46 (s, 3H); 1.38 (t, J=7.0 Hz, 3H)

Compound M: CDCl$_3$

δ 7.1–8.2 (m, 7H); 6.9 (s, 1H); 5.5 (s, 2H); 4.0 (q, J=7.3 Hz, 2H); 2.8 (q, J=7.7 Hz, 2H); 2.6 (s, 3H); 2.5 (s, 3H); 1.3 (t, J=7.7 Hz, 3H); 0.7 (t, J=7.3 Hz, 3H)

Compound N-Na salt: DMSO-$d_6$

δ 7.1–7.9 (m, 8H); 5.50 (s, 2H); 3.39 (s, 2H); 2.40 (s, 3H); 2.23 (s, 3H)

Compound O-Na salt: DMSO-$d_6$

δ 7.1–7.9 (m, 8H); 5.52 (s, 2H); 2.55 (s, 3H); 2.54 (s, 3H); 2.40 (s, 3H)

Experimental Example 1

Inhibition of binding of angiotensin II to rat smooth muscle cells

The compound of the present invention and $^{125}$I-Tyr$^4$-angiotensin II (0.25 μCi, 150 μl, "NEX-105", manufactured by NEX Corp., hereinafter abbreviated as $^{125}$I-AII) were added to smooth muscle cells from rat aorta, and the mixture was incubated at room temperature for 1 hour. Unbound $^{125}$I-AII was washed with PBS (phosphate buffer), and the radioactivity of the bound $^{125}$I-AII was measured, from which the inhibitory action (IC$_{50}$) of each compound of the present invention as prepared in respective Examples on the binding of angiotensin II to the receptor was determined. The results are as follows.

IC$_{50}$ of the compound of Example 4: $4.3 \times 10^{-9}$M
IC$_{50}$ of the compound of Example 5: $4.0 \times 10^{-8}$M
IC$_{50}$ of the compound of Example 6: $1.9 \times 10^{-8}$M
IC$_{50}$ of the compound of Example 7: $1.3 \times 10^{-7}$M
IC$_{50}$ of the compound of Example 9: $2.5 \times 10^{-9}$M
IC$_{50}$ of the compound of Example 10: $7.2 \times 10^{-7}$M
IC$_{50}$ of the compound of Example 12: $6.0 \times 10^{-8}$M
IC$_{50}$ of the compound of Example 14: $2.5 \times 10^{-9}$M
IC$_{50}$ of the compound of Example.16: $6.7 \times 10^{-9}$M
IC$_{50}$ of the compound of Example 18: $2.0 \times 10^{-9}$M
IC$_{50}$ of the compound of Example 20: $1.4 \times 10^{-9}$M
IC$_{50}$ of the compound of Example 21: $1.1 \times 10^{-9}$M
IC$_{50}$ of the compound of Example 22: $1.8 \times 10^{-9}$M
IC$_{50}$ of the compound of Example 23: $3.1 \times 10^{-9}$M
IC$_{50}$ of the compound of Example 24: $8.0 \times 10^{-10}$M
IC$_{50}$ of the compound of Example 25: $7.2 \times 10^{-10}$M Formulation Example 1: Tablets

| | |
|---|---|
| (1) Compound (1) of the invention | 10 mg |
| (2) Fine particle for direct compression No. 209 (manufactured by Fuji Kagaku Corp.) | 46.6 mg |
| magnesium aluminate metasilicate | 20% |
| corn starch | 30% |
| lactose | 50% |
| (3) Crystalline cellulose | 24.0 mg |
| (4) Carboxylmethyl cellulose · calcium | 4.0 mg |
| (5) Magnesium stearate | 0.4 mg |

(1), (3), and (4) are previously passed through a 100-mesh sieve. (1), (3), (4), and (2) are respectively dried to a certain moisture content, and kneaded in a kneader at the above-mentioned weight ratio. (5) is then added to the uniform powder mixture and mixed for a short time (30 sec), and the powder mixture is compressed into tablets (pounder: 6.3 mm Φ, 6.0 mmR) of 85 mg per tablet.

The obtained tablets may be coated with an enteric film coating agent such as poly(vinyl acetal) diethylaminoacetate or an edible colorant conventionally employed on demand.

Formulation Example 2: Capsules

| | |
|---|---|
| (1) Compound (1) of the invention | 50 g |
| (2) Lactose | 935 g |
| (3) Magnesium stearate | 15 g |

The above ingredients are weighed and uniformly mixed. The powder mixture is packed in hard gelatin capsules by 200 mg.

Formulation Example 3: Injections

| | |
|---|---|
| (1) Compound (1) of the invention · hydrochloride | 5 mg |
| (2) Sucrose | 100 mg |
| (3) Physiological saline | 10 ml |

A mixed solution of the above ingredients is filtered through a membrane filter, and further sterilized by filtration. Then, the filtrate is dispensed to a vial aseptically and nitrogen gas is charged, after which the vial is sealed to give an intravenous injection.

What is claimed:

1. An isoindazole compound of the formula (1)

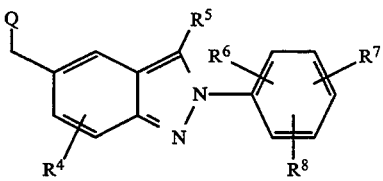

(1)

where Q is a heterocyclic derivative of the formula (2) or (3)

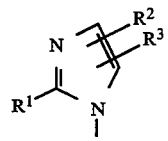

(2)

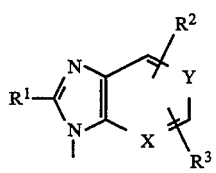

(3)

wherein in the formulas (1), (2), and (3), R–R⁸, X, and Y stand for the following:

$R^1$ is lower alkyl, halo-lower alkyl, cyclo-lower alkyl, alkenyl, alkoxyl, alkoxy-lower alkyl, or alkylthio;

$R^2$ and $R^3$ may be the same or different, and each is independently hydrogen atom, halogen atom, lower alkyl, halo-lower alkyl, cyclo-lower alkyl, alkenyl, alkoxyl, —$C_mF_{2m+1}$, —$(CH_2)_nR^9$, or —$(CH_2)_pCOR^{10}$;

$R^4$ and $R^5$ may be the same or different, and each is independently hydrogen atom, halogen atom, lower alkyl, alkoxyl, or —$C_mF_{2m+1}$;

$R^6$ is carboxyl, —$COOR^{11}$, —$CONH_2$, cyano, —$SO_3H$, —$SO_2NH_2$, —$NHSO_2CF_3$, or C-bonded tetrazolyl;

$R^7$ and $R^8$ may be the same or different, and each is independently hydrogen atom, halogen atom, lower alkyl, alkoxyl, or —$C_mF_{2m+1}$; and X and Y may be the same or different, and each is independently CH or nitrogen atom; in which the aforementioned $R^9$–$R^{11}$, m, n, and p designate the following:

$R^9$ is hydroxyl or alkoxyl;

$R^{10}$ is hydrogen atom, hydroxyl, lower alkyl, or alkoxyl;

$R^{11}$ is lower alkyl, alkenyl, cyclo-lower alkyl, aryl, or aralkyl;

m is an integer of 1–6;

n is an integer of 1–4;

p is an integer of 0–4; or a salt thereof.

2. The isoindazole compound as claimed in claim 1, wherein, in the formula (1), Q is a heterocyclic derivative of the formula (2) or (3), in which $R^1$ is lower alkyl or alkenyl, $R^2$ and $R^3$ may be the same or different and each is independently hydrogen atom, halogen atom, lower alkyl —$(CH_2)_nR^9$, or —$(CH_2)_pCOR^{10}$ (in which $R^9$ is hydroxyl or alkoxyl, $R^{10}$ is hydrogen atom, hydroxyl, or alkoxyl, n is an integer of 1–4, and p is an integer of 0–4); or a salt thereof.

3. The isoindazole compound as claimed in claim 1 or 2, wherein, in the formula (1), $R^4$ is hydrogen atom, and $R^5$ is hydrogen atom or halogen atom, or a salt thereof.

4. The isoindazole compound as claimed in any one of claims 1 to 3, wherein, in the formula (1), $R^6$ is carboxyl or C-bonded tetrazolyl, or a salt thereof.

5. The isoindazole compound as claimed in any one of claims 1 to 4, wherein, in the formula (1), $R^7$ and $R^8$ may be the same or different and each is independently hydrogen atom, fluorine atom, chlorine atom, lower alkyl, or alkoxyl, or a salt thereof.

6. The isoindazole compound as claimed in claim 1, wherein, in the formula (1), Q is a heterocyclic derivative of the formula (2), in which $R^1$ is lower alkyl or alkenyl, $R^2$ is chlorine atom, and $R^3$ is —$(CH_2)_nR^9$ or —$(CH_2)_pCOR^{10}$ (in which $R^9$ is hydroxyl or alkoxyl, R is hydrogen atom, hydroxyl, or alkoxyl, n is an integer of 1–4, and p is an integer of 0–4), or a salt thereof.

7. The isoindazole compound as claimed in claim 1, wherein, in the formula (1), Q is a heterocyclic derivative of the formula (2), in which $R^1$ is lower alkyl, $R^2$ is chlorine atom, $R^3$ is —$(CH_2)_nR^9$ or —$(CH_2)_pCOR^{10}$ (in which $R^9$ is hydroxyl, $R^{10}$ is hydrogen atom, hydroxyl, or alkoxyl, n is an integer of 1, and p is an integer of 0 or 1), $R^4$ is hydrogen atom, $R^5$ is hydrogen atom, fluorine atom, chlorine atom, or bromine atom, $R^6$ is carboxyl or C-bonded tetrazolyl, and $R^7$ and $R^8$ may be the same or different and each is independently hydrogen atom, fluorine atom, chlorine atom, or lower alkyl, or a salt thereof.

8. The isoindazole compound as claimed in any one of claims 1 to 5, wherein, in the formula (1), Q is a heterocyclic derivative of the formula (3), in which X is nitrogen atom and Y is CH, or a salt thereof.

9. The isoindazole compound as claimed in claim 1, wherein, in the formula (1), Q is a heterocyclic derivative of the formula (3), in which $R^1$ is lower alkyl, $R^2$ and $R^3$ may be the same or different and each is independently hydrogen atom, lower alkyl, —$(CH_2)_nR^9$, or —$(CH_2)_pCOR^{10}$ (in which $R^9$ is hydroxyl, $R^{10}$ is hydrogen atom, hydroxyl, or alkoxyl, n is 1, and p is 0 or 1), X is nitrogen atom, Y is CH, $R^4$ is hydrogen atom, $R^5$ is hydrogen atom, fluorine atom, chlorine atom, or bromine atom, $R^6$ is carboxyl or C-bonded tetrazolyl, and $R^7$ and $R^8$ may be the same or different and each is independently hydrogen atom, fluorine atom, chlorine atom, or lower alkyl, or a salt thereof.

10. The isoindazole compound as claimed in claim 1 which selected from the group consisting of 1-[3-bromo-2-(2-carboxyphenyl)-2H-indazol-5-yl]methyl-2-butyl-4-chloro-5-(hydroxymethyl)-1H-imidazole, 1-{[3-bromo-2-[2-(1H-tetrazol-5-yl)phenyl]-2H-indazol-5-yl]methyl}-2-butyl-4-chloro-5-(hydroxymethyl)-1H-imidazole, 2-butyl-3-[3-bromo-2-(2-carboxyphenyl)-2H-indazol-5-yl]methyl-3H-imidazo[4,5-b]pyridine sodium salt, sodium 3-[3-bromo-2-(2-carboxyphenyl)-2H-indazol-5-yl]methyl-5,7-dimethyl-2-ethyl-3H-imidazo[4,5-b]pyridine, 3-{[3-bromo-2-[2-(1H-tetrazol-5-yl)phenyl]-2H-indazol-5-yl]methyl}-2-ethyl-5,7-dimethyl-3H-imidazo[4,5-b]pyridine, and 3-{[3-bromo-2-[2-(1H-tetrazol-5-yl)phenyl]-2H-indazol-5-yl]methyl}-2-butyl-3H-imidazo[4, 5-b]pyridine, or a salt thereof.

11. A pharmaceutical composition comprising the isoindazole compound as claimed in claim 1 or a salt thereof, and pharmaceutically acceptable carriers.

12. The pharmaceutical composition as claimed in claim 11, wherein the pharmaceutical composition is an angiotensin II antagonist.

13. The pharmaceutical composition as claimed in claim 11, wherein the pharmaceutical composition is an agent for the treatment of circulatory diseases.

14. The pharmaceutical composition as claimed in claim 11, wherein the pharmaceutical composition is an agent for the treatment of hypertension or heart failure.

15. A method for antagonizing angiotensin II, which comprises use of the isoindazole compound as claimed in claim 1 or a salt thereof.

16. A method for the treatment of circulatory diseases, which comprises use of the isoindazole compound as claimed in claim 1 or a salt thereof.

17. A method for the treatment of hypertension or heart failure, which comprises use of the isoindazole compound as claimed in claim 1 or a salt thereof.

* * * * *